US012595234B2

(12) United States Patent
Das et al.

(10) Patent No.: US 12,595,234 B2
(45) Date of Patent: Apr. 7, 2026

(54) BIOACTIVE BENZOCYCLOHEPTENE ANALOGUES FROM HIMACHALENES AND ITS APPLICATIONS

(71) Applicant: Council of Scientific and Industrial Research, New Delhi (IN)

(72) Inventors: Pralay Das, Palampur (IN); Yamini, Palampur (IN); Richa Bharti, Palampur (IN); Shankar Ram, Palampur (IN); Vijay Kumar Bhardwaj, Palampur (IN); Rituraj Purohit, Palampur (IN); Damanpreet Singh, Palampur (IN); Prince Anand, Palampur (IN); Yogendra S Padwad, Palampur (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 415 days.

(21) Appl. No.: 18/032,732

(22) PCT Filed: Oct. 19, 2021

(86) PCT No.: PCT/IN2021/050993
§ 371 (c)(1),
(2) Date: Apr. 19, 2023

(87) PCT Pub. No.: WO2022/085023
PCT Pub. Date: Apr. 28, 2022

(65) Prior Publication Data
US 2023/0382860 A1 Nov. 30, 2023

(30) Foreign Application Priority Data
Oct. 19, 2020 (IN) ............................ 202011045582

(51) Int. Cl.

| | |
|---|---|
| ***C07D 209/94*** | (2006.01) |
| ***C07C 311/16*** | (2006.01) |
| ***C07C 317/10*** | (2006.01) |
| ***C07C 317/14*** | (2006.01) |
| ***C07D 221/18*** | (2006.01) |
| ***C07D 307/93*** | (2006.01) |

(52) U.S. Cl.
CPC .......... *C07D 209/94* (2013.01); *C07C 311/16* (2013.01); *C07C 317/10* (2013.01); *C07C 317/14* (2013.01); *C07D 221/18* (2013.01); *C07D 307/93* (2013.01); *C07C 2602/12* (2017.05)

(58) Field of Classification Search
CPC .. C07D 209/94; C07D 221/18; C07D 307/93; C07C 311/16; C07C 317/10; C07C 317/14; C07C 2602/12
See application file for complete search history.

(56) References Cited

U.S. PATENT DOCUMENTS

| | | | | |
|---|---|---|---|---|
| 4,148,919 | A | 4/1979 | Nedelec et al. | |
| 5,252,589 | A * | 10/1993 | Ozeki | A61P 15/00 544/146 |
| 6,211,193 | B1 | 4/2001 | Remiszewski et al. | |
| 6,218,401 | B1 | 4/2001 | Afonso et al. | |
| 6,759,412 | B2 | 7/2004 | Strobel et al. | |
| 7,256,204 | B2 | 8/2007 | Kato et al. | |
| 8,877,779 | B2 | 11/2014 | Nakano et al. | |
| 2009/0099250 | A1 | 4/2009 | Ralf et al. | |

FOREIGN PATENT DOCUMENTS

| | | | |
|---|---|---|---|
| CH | 633253 | A5 | 11/1982 |
| WO | 200230422 | A1 | 4/2002 |
| WO | 2009/092284 | * | 7/2009 |
| WO | 2009092284 | A1 | 7/2009 |

OTHER PUBLICATIONS

Stark, Pharmacology, vol. 23, 2015, pp. 82-91. (Year: 2015).*
Zhang, BMC Cancer, 2022, vol. 11(190), 1-11. (Year: 2022).*
Rommel, et al., "PI3K$\delta$ and PI3K$_\gamma$: partners in crime in inflammation in rheumatoid arthritis and beyond?", Nature Reviews, Immunology, vol. 7, pp. 191-201, Mar. 2007.
Campa, et al., "Inhalation of the prodrug PI3K inhibitor CL27c improves lung function in asthma and fibrosis", Nature Communications, pp. 1-16, 2018.
Hawkins, et al., "PI3K signalling in inflammation", Biochimica et Biophysica Acta, vol. 1851, pp. 882-897, 2015.
Ghigo, et al., "PI3K inhibition in inflammation: Toward tailored therapies for specific diseases", BioEssays, vol. 32, pp. 185-196, 2010.
Soni, et al., "MAPKAPK2: the master regulator of RNA-binding proteins modulates transcript stability and tumor progression", Journal of Experimental & Clinical Cancer Research, vol. 38, No. 121, pp. 1-18, 2019.
Russo, et al., "Phosphoinositide 3-kinase $_\gamma$ plays a critical role in bleomycin-induced pulmonary inflammation and fibrosis in mice", Journal of Leukocyte Biology, vol. 89, pp. 269-282, Feb. 2011.
Cantley, et al., "Specificity in recognition of phosphopeptides by src-homotology 2 domains", Journal of Cell Science, Supplement 18, pp. 121-125, 1994.

(Continued)

*Primary Examiner* — D Margaret M Seaman
(74) *Attorney, Agent, or Firm* — DINSMORE & SHOHL LLP

(57) ABSTRACT

Functionalized benzocycloheptenes are one of the most important classes of bicyclic framework that have been investi-gated in different areas of biological activities. The claimed invention provides preparations of benzocycloheptene analogues, inhibitors of PI3K and MK2, pharmaceutical compositions containing them and their use in therapy. The compounds of Formula I, II, III, IV, V and VI may be used as anti type 2 diabetes, antipyretic, anti-inflammatory, anti-epileptic, anticancer, antiulcer, CNS-stimulant, and CNS-depressant. These benzocycloheptene derivatives are useful in treatment of PI3K and MK2 related disorders.

10 Claims, 6 Drawing Sheets

(56) References Cited

OTHER PUBLICATIONS

Yuasa-Kawada, et al., "Deubiquitinating enzyme USP33/VDU1 is required for Slit signaling in inhibiting breast cancer cell migration", PNAS, vol. 106, No. 34, pp. 14530-14535, Aug. 25, 2009.
Cantley, "The Phosphoinositide 3-Kinase Pathway", Viewpoint, Mapping Cellular Signaling, vol. 296, pp. 1655-1657, May 2002.
Gurgis, et al., "Mitogen-Activated Protein Kinase-Activated Protein Kinase 2 in Neuroinflammation, Heat Shock Protein 27 Phosphorylation, and Cell Cycle: Role and Targeting", Molecular Pharmacology, vol. 85, pp. 345-356, Feb. 2014.
Maruyama, et al., "Stress-Activated MAP Kinase Cascades in Cellular Senescence", Current Medicinal Chemistry, vol. 16, pp. 1229-1235, 2009.
Jackson, et al., "Kinase Activity, Heat Shock Protein 27 Phosphorylation, and Lung Epithelial Cell Glutathione", Experimental Lung Research, vol. 34, pp. 245-262, 2008.
Pearson, et al., "Mitogen-Activated Protein (MAP) Kinase Pathways: Regulation and Physiological Functions", Endocrine Reviews, vol. 22, No. 2, pp. 153-183, 2001.
Pomerance, et al., "High-level expression, activation, and subcellular localization of p38-MAP kinase in thyroid neoplasms", Journal of Pathology, vol. 409, pp. 298-306, 2006.
Kotlyarov, et al., "Distincy Cellular Functions of MK2", Molecular and Cellular Biology, vol. 22, No. 13, pp. 4827-4835, 2002.
Rogalla, et al., "Cell Biology and Metabolism: Regulation of Hsp27 Oligomerization, Chaperone Function, and Protective Activity against Oxidative Stress/Tumor Necrosis Factor a by Phosphorylation", The Journal of Biological Chemistry, vol. 274, pp. 18947-18956, 1999.
Cannell, et al., "A Pleiotropic RNA-Binding Protein Controls Distinct Cell Cycle Checkpoint to Drive Resistance of p53Defective Tumors to Chemotherapy", Cancer Cell, vol. 28, pp. 1-16, Nov. 2015.
Winzen, et al., "The p38 MAP kinase pathway signals for cytokine-induced mRNA stabilixation via MAP kinase-activated protein kinase 2 and an AU-rich region-targeted mechanism", the EMBO Journal, vol. 18, No. 18, pp. 4969-4980, 1999.
Menon, et al., "$P38^{MAPK}$/MK2-dependent phosphorylation controls cytotoxi RIPK1 signalling in inflammation and infection", Nature Cell Biology, pp. 1-29, 2017.
Manke, et al., "MAPKAP Kinase-2 is a Cell Cycle Checkpoint Kinase that Regulates the G2/M Transition and S Phase Progression in Response to UV Irradiation", Molecular Cell, vol. 17, pp. 37-48, 2005.
Weber, et al., "HDM2 phosphorylation by MAPKAP kinase 2", Oncogene, vol. 24, pp. 1965-1972, 2005.
Erdem, et al., "Loss of MKK3 and MK2 Copy Numbers in Non-Small Cell Lung Cancer", Journal of Cancer, vol. 7, pp. 512-516, 2016.
Kumar, et al., "P38 Mitogen-Activated Protein Kinase-Driven MAPKAPK2 Regulates Invasion of Bladder Cancer by Modulationof MMP-2 and MMP-9 Activity", Cancer Research, Tumor and Stem Cell Biology, vol. 70, No. 2, pp. 832-842, 2010.
Henriques, et al., "Mesenchymal MAPKAPK2/HSP27 drives intestinal carcinogenesis", PNAS, pp. 1-10, 2018.
Cheruku, et al., "Transforming growth factor-β, MAPK and Wnt signaling interactions in colorectal cancer", EuPA Open Proteomics, vol. 8, pp. 104-115, 2015.
Hayes, et al., "p38 MAP kinase modulates Smad-dependent changes in human prostate cell adhesion", Oncogene, vol. 22, pp. 4841-4850, 2003.
Liu, et al., "A Functional Copy-Number Variation in MAPKAPK2 Predicts Risk and Prognosis of Lung Cancer", The American Journal of Human Genetics, vol. 91, pp. 384-390, Aug. 2012.
Soni, et al., MAPKAPK2 plays a crucial role in the progression of head and neck squamous cell carcinoma by regulating transcript stability, Journal of Experimental & Clinical Cancer Research, vol. 38, No. 175, pp. 1-13, 2019.
Correa, et al., "The Role of p38 MAPK and Its Substrates in Neuronal Plasticity and Neurodegenerative Disease", Journal of Signal Transduction, pp. 1-13, 2012.
Culbert, et al., "MAPK-activated Protein Kinase 2 Deficiency in Microglia Inhibits Pro-Inflammatory Mediator Release and Resultant Neurotoxicity", The Journal of Biological Chemistry, vol. 238, No. 33, pp. 23658-23667, Aug. 2006.
Shafiq, et al., "Inhibition of Mitogen-Activated Protein Kinase (MAPK)-Activated Protein Kinase 2 (MK2) is Protective in Pulmonary Hypertension", Hypertension, vol. 77, pp. 1248-1259, 2021.
Lopes, et al., "Cell Permeant Peptide Analogues of the Small Heat Shock Protein, HSP20, Reduce TGF-β1-Induced CTGF Expression in Keloid Fibroblasts", Journal of Investigative Dermatology, vol. 129, pp. 590-599, 2009.
Liang, et al., "Mitogen-activated Protein Kinase-activated Protein Kinase 2 Inhibition Attenuates Fibroblast Invasion and Severe Lung Fibrosis", MKS Contributes to Lung Fibrosis, pp. 41-49, 2018.
Vittal, et al., "Peptide-Mediated Inhibition of Mitogen-Activated Protein Kinase-Activated Protein Kinase-2 Ameliorates Bleomycin-Induced Pulmonary Fibrosis", American Journal of Respiratory Cell and Molecular Biology, vol. 49, pp. 47-57, 2013.
Gorska, et al., "MK2 controls the level of negative feedback in the $NF-^{K}B$ pathway and is essential for vascular permeability and airway inflammation", JEM Article, vol. 204, No. 7, pp. 1637-1652, 2007.
Hegen, et al., "MAPKAP Kinase 2-Deficient Mice Are Resistant to Collagen-Induced Arthritis", The Journal of Immunology, pp. 1913-1917, 2006.
Jagavelu, et al., "Systemetic Deficiency of the MAP Kinase-Activated Protein Kinase 2 Reduces Atherosclerosis in Hypercholesterolemic Mice", Circulation Research, pp. 1-18, 2007.
Alam, et al., "Targeting neuronal MAPK14/p38α activity to modulate autophagy in the Alzheimer disease brain", Autophagy, vol. 12, No. 12, pp. 2516-2520, 2016.
Liu, et al., "Synthesis of benzocycloheptene derivatives as CCR5 antagonists with potent anti-HIV activity", ScienceDirect, vol. 19, pp. 428-430, 2008.
Adam, et al., "Reactions of Benzocycloheptenes with Dienophiles", Chem. Ber., pp. 383-386, 1991.
Tandon, et al., "Chemo-and steroselective synthesis of benzocycloheptene and 1-benzoxepin derivatives as α-sympathomimetic and anorexigenic agents", ScienceDirect, Bioorganic & Medicinal Chemistry Letters, vol. 14, pp. 2867-2870, 2004.
Shiraishi, et al., "Discovery of Novel, Potent, and Selective Small-Molecule CCR5 Antagonists as Anti-HIV-1 Agents: Synthesis and Biological Evaluation of Anilide Derivatives with a Quaternary Ammonium Moiety", J. Med. Chem., vol. 43, pp. 2049-2063, 2000.
Sriram, et al., "Design, synthesis and biological evaluation of dihydronaphthalene and benzosuberene analogs of the combretastatins as inhibitors of tubulin polymerization in cancer chemotherapy", Bioorganic & Medicinal Chemistry, vol. 16, pp. 8161-8171, 2008.
Chen, et al., "Synthesis of 3-methoxyphenyl)-6,7-dihydro-5H-benzo[7]annulen-4-ol, a potent antineoplastic benzosuberene derivative for anti-cancer chemotherapy", Tetrahedron Letters, vol. 53, pp. 64-66, 2012.
Pettit, et al., "Isolation and structure of the strong cell growth and tubulin inhibitor combretastatin A-4[1]", Short Communications, Experientia, vol. 45, pp. 209-211, 1989.
Tanpure, et al., "An amino-benzosuberene analogue that inhibits tubulin assembly and demonstrates remarkable cytotoxicity", MedChemComm, vol. 3, pp. 720-724, 2012.
Maximov, et al., "Influence of the Length and Positioning of the Antiestrogenic Side Chain of Endoxifen and 4-Hydroxytamoxifen on Gene Activation and Growth of Estrogen Receptor Positive Cancer Cells", Journal of Medicinal Chemistry, vol. 57, pp. 4569-4583, 2014.
Liu, "Synthesis of oxygen heterocycles via alkynyltungsten compounds", Pure Appl., Chem., vol. 73, No. 2, pp. 265-269, 2001.
Reddy, et al., "Synthesis and Antimicrobial Activity of Novel Phosphorus heterocycles with Exocyclic P—C Link", Chem. Parm. Bull, vol. 52, No. 3, pp. 307-310, 2004.
Garcia-Valverde, et al., "Special Issue: Sulfur-Nitrogen Heterocycles", Molecules, vol. 10, pp. 318-320, 2005.

(56) References Cited

OTHER PUBLICATIONS

Abdel-Hafez, "Selenium containing heterocycles: Synthesis, anti-inflammatory, analgesic and anti-microbial activities of some new 4-cyanopyridazine-3(2H)selenone derivatives", ScienceDirect, vol. 43, pp. 1971-1977, 2008.
Vitaku, et al., "Analysis of the Structural Diversity, Substitution Patterns, and Frequency of Nitrogen Heterocycles among U.S. FDA Approved Pharmaceuticals", Journal of Medicinal Chemistry, vol. 57, pp. 10257-10274, 2014.
Crielaard, et al., "A polymeric colchicinoid prodrug with reduced toxicity and improved efficacy for vascular disruption in cancer therapy", International Journal of Nanomedicine, vol. 6, pp. 2697-2703, 2011.
Joseph, et al., "Synthesis and in Vitro Cytotoxic Evaluation of N-Substituted Benzo[5,6]cyclohepta[b]indoles", Chem. Pharm. Bull, vol. 48, No. 12, pp. 1872-1876, 2000.
Noshi, et al., "Conversion of Cyclic Vinyl Sulfones to Transposed Vinyl Phosphonates", J. Am. Chem. Soc., vol. 129, pp. 11242-11247, 2007.
Desrosiers, et al., "Catalytic Enantioselective Reduction of β,β-Disubstituted Vinyl Phenyl Sulfones by Using Bisphosphine Monoxide Ligands", Asymmetric Catalysis, vol. 46, pp. 5955-5957, 2007.
Pandey, et al., "Use of Enantiomerically Pure 7-Azabicyclo[2.2.1]heptan-2-ol as a Chiral Template for the Synthesis of Aminocyclitols", Organic Letters, vol. 10, No. 15, pp. 3611-3614, 2008.
Oh, "A Rapid Synthesis of the Biotin Core through a Tandem Michael Reaction", Organic Letters, vol. 9, No. 16, pp. 2973-2975, 200.
Nishimura, et al., "Effect of Chiral Diene Ligands in Rhodium-Catalyzed Asymmetric Addition of Arylboronic Acids to $\alpha_1\beta$-Unsaturated Sulfonyl Compounds", Journal of the American Chemical Society, vol. 134, pp. 9086-9089, 2012.
Duarte, et al., "Mechanisms for blood pressure lowering and metabolic effects of thiazide and thiazide-like diuretics", Review, Expert Reviews, vol. 8, No. 6, pp. 793-802, 2010.
Rais-Bahrami, et al., "Use of Furosemide and Hearing Loss in neonatal Intensive Care Survivors", American Journal of Perinatology, vol. 21, No. 6, pp. 329-332, 2004.
Desrosiers, et al., "Catalytic Enantioselective Addition of Diorganozinc Reagents to Vinyl Sulfones", Organic Letters, vol. 10, No. 11, pp. 2315-2318, 2008.
Uttamchandani, et al., "Activity-based fingerprinting and inhibitor discovery of cysteine proteases in a microarray", Chem. Communication., pp. 1518-1520, 2007.
Wang, et al., "Multicomponent Strategy to Pyrazolo[3,4-e]indolizine Derivatives under Microwave Irradiation", The Journal of Organic Chemistry, vol. 80, pp. 8435-8442, 2015.
Hof, et al., "Starving the Malaria Parasite: Inhibitors Active against the Aspartic Proteases Plasmepsins I, II, and IV", Enzyme Inhibitors, vol. 45, pp. 2138-2141, 2006.
Forristal, "The chemistry of α,β-unsaturated sulfoxides and sulfones: an update", Journal of Sulfur Chemistry, Review Article, vol. 26, No. 2, pp. 163-195, Apr. 2005.
Williams, et al., "Sulindac Sulfide, but Not Sulindac Sulfone, Inhibits Colorectal Cancer Growth", Neoplasia, vol. 1, No. 2, pp. 170-176, Jun. 1999.
Schellhammer, "An evaluation of bicalutamide in the treatment of prostate cancer", Drug Evaluation, Expert Opinion, vol. 3, No. 9, pp. 1313-1328, 2002.
Billard, et al., "Diphenylsulfone Muscarinic Antagonists: Piperidine Derivatives with High $M_2$ Selectivity and Improved Potency", Bioorganic & Medicinal Chemistry Letters, vol. 10, pp. 2209-2212, 2010.
Padmavathi, et al., "Synthesis and antimicrobial activity of novel sulfone-linked bis heterocycles", ScienceDirect, European Journal of Medicinal Chemistry, vol. 43, pp. 917-924, 2008.
Konduru, et al., "Synthesis and antibacterial and antifungal evaluation of some chalcone based sulfones and bisulfones", European Journal of Medicinal Chemistry, vol. 59, pp. 23-30, 2013.
Todd, et al., "An Update of its Pharmacology and Therapeutic Efficacy in Rheumatic Diseases", Tenoxicam, Drugs, vol. 41, No. 4, pp. 625-646, 1991.
Lee, et al., "A Review of its Pharmacodynamic and Pharmacokinetic Properties, and Therapeutic Potential in Rheumatic Diseases and Pain States", Piroxicam-β-Ctclodextrin, Drug Evaluation, vol. 48, No. 6, pp. 907-929, 1994.
Faget, et al., "The Promin Treatment of Leprosy, a Progress Report", Reprinted Article, International Journal of Leprosy, vol. 34, No. 3, pp. 298-310, 1966.
Mitchell, et al., "Mesotrione: a new selective herbicide for use in maize", Pest Management Science, vol. 57, pp. 120-128, 2001.
Boger, "Mode of Action for Chloroacetamides and Functionally Related Compounds", Journal Pestic. Sci., vol. 28, pp. 324-329, 2003.
Jean, et al., "Classes of phosphoinositide 3-kinases at a glance", The Company of Biologists, Journal of Cell Science, vol. 127, pp. 923-928, 2014.
Liu, et al., "Targeting the phosphoinositide 3-kinase pathway in cancer", Nature Reviews, Drug Discovery, vol. 8, pp. 627-644, Aug. 2009.
Carracedo, et al., "The PTEN-PI3K pathway: of feedbacks and cross-talks", Oncogene, vol. 27, pp. 5527-5541, 2008.
Stark, et al., "PI3K inhibitors in inflammation, autoimmunity and cancer", ScienceDirect, Current Opinion in Pharmacology, vol. 23, pp. 82-91, 2015.
Fruman, et al., "PI3K and cancer:lessons, challenges and opportunities", Reviews, vol. 13, pp. 140-156, Feb. 2014.
Thomas, et al., "High-throughput oncogene mutation profiling in human cancer", Nature Genetics Letters, vol. 39, No. 3, pp. 347-352, Mar. 2007.
Samuels, et al., "High Frequency of Mutations of the PIK3CA Gene in Human Cancers", Brevia, vol. 304, pp. 554-555, Apr. 2004.
Wood, et al., "The Genomic Landscapes of Human Breast and Colorectal Cancers", Research Articles, Science, vol. 318, pp. 1108-1113, Nov. 2007.
McLendon, et al., "Comprehensive genomic characterization defines human glioblastoma genes and core pathways", Nature Articles, vol. 455, pp. 1061-1068, Oct. 2008.
Ding, et al., "Somatic mutations affect key pathways in lung adenocarcinoma", Nature Articles, vol. 455, pp. 1069-1075, Oct. 2008.
Di Cristofano, et al., "Pten and $p27^{KIP1}$ cooperate in prostate cancer tumor suppression in the mouse", Nature Genetics, vol. 27, pp. 222-224, Feb. 2001.
Parsons, et al., "An Integrated Genomic Analysis of Human Glioblastoma Multiforme", Science Research Articles, vol. 321, pp. 1807-1812, Sep. 2008.

* cited by examiner

BIOACTIVE BENZOCYCLOHEPTENE ANALOGUES FROM HIMACHALENES AND ITS APPLICATIONS

CROSS REFERENCES TO RELATED APPLICATIONS

This application is a national-stage application under 35 U.S.C. § 371 of International Application No. PCT/IN2021/050993, filed Oct. 19, 2021, which International Application claims benefit of priority to Indian patent application Ser. No. 202011045582, filed Oct. 19, 2020.

FIELD OF THE INVENTION

The present invention relates to new compounds of formula (I), (II), (III), (IV), (V), (VI) and (VII) wherein $R^1$, $R^2$, $R^3$, $R^4$, $R^5$ and X, Y and Z are as defined herein, and their applications in treatment of PI3K and MK2 related disorders for use as antipyretic, anti-inflammatory, antiepileptic, anticancer, antiulcer diseases, CNS-stimulant, and CNS-depressant activities and in the manufacture of medicines/drugs for such treatment.

BACKGROUND OF THE INVENTION

Benzocycloheptene is a bicyclic skeleton that comprises of ring formation as one of the pivotal transformation [Y. Liu, J. Su, J. H. Xiao, S. B. Jiang, H. Lu, W. Zhong, L. L. Wang, X. H. and S. Li, Chinese *Chem. Lett.,* 2008, 19, 428-430; W. Adam, M. Balci, Z. Ceylan and R. F., Chem. Ber., 1991, 124, 383-386]. Benzocycloheptene and their derivatives are attractive biological targets in theoretical chemistry and pharmaceutical sciences, and coordination chemistry [V. K. Tandon, K. A. Singh, A. K. Awasthi, J. M. Khanna, B. Lal and N. Anand, *Bioorg. Med. Chem. Lett.,* 2004, 14, 2867-2870; M. Shiraishi, Y. Aramaki, M. Seto, H. Imoto, Y. Nishikawa, N. Kanzaki, M. Okamoto, H. Sawada, O. Nishimura, M. Baba and M. Fujino, *J Med Chem.,* 2000 43, 2049-2063; R. Wyrwa, O. Peters, R. Bohlmann, P. Droescher, K. Prellle, K. H. Fritzemeier, H. P. Muhn, Patent US2009/0099250 A1, 2009]. Among benzocycloheptene, amine substituted benzocycloheptene have drawn much attention and intense research activity because of their profound pharmacological potential. These were reported for the treatment of cancer [M. Sriram, J. J. Hall, N. C. Grohmann, T. E. Strecker, T. Wootton, A. Franken, M. L. Trawick and K. G. Pinney, *Bioorg. Med. Chem.,* 2008, 16, 8161-8171; H. Strobel, P. Wohlfart, U.S. Pat. No. 6,759,412 B2, 2004; Z. Chen, C. J. O'Donnell and A. Maderna, *Tetrahedron Lett.,* 2012, 53, 64-66], mental disorder [M. Nakano, M. Minoguchi, T. Hanano, S.-I. Ono, H. Horiuchi, K. Teshima, US Patent, 0120841A1, 2010], cardiovascular [CV. Amsterdam, Patent Application no. WO/2002/030422A1, 2002], neurodegenerative [K. Kato, J. Terauchi, H. Fukumoto, M. Kakihana, Patent U.S. Pat. No. 7,256, 204B2, 2007], antidepressant [L. Nedelec, A. Pierdet, C. Dumont, M-H. Kannengiesser, Patent U.S. Pat. No. 4,148, 919, 1979] and also work as antiarrhythmic [M. Baumgarth, I. Lues, K-O Minck,. N. Beier, Patent U.S. Pat. No. 5,495, 022, 1996] and antiparkinson agents. The arylated benzosuberene derivatives is established in medicinal chemistry as anticancer agents because of their structural reminiscence to colchicine and combretastatin CA4 and CA1 [G. R. Pettit, S. B. Singh, C. M. Hamel-Lin, D. S. Alberts and D. Garcia-Kendall, *Experientia.,* 1989, 45, 209]. The major synthetic methods for benzocycloheptene synthesis suffered from some disadvantages like the tedious reaction conditions [M. Sriram, J. J. Hall, N. C. Grohmann, T. E. Strecker, T. Wootton, A. Franken, M. L. Trawick and K. G. Pinney, *Bioorg. Med. Chem.,* 2008, 16, 8161-8171.], difficulty to prepare the substituted congeners, the commercial available starting materials [R. P. Tanpure, C. S. George, M. Sriram, T. E. Strecker, J. K. Tidmore, E. Hamel, A. K. Charlton-Sevcika, D. J. Chaplin, M. L. Trawick and K. G. Pinney, *Med. Chem. Commun.,* 2012, 6, 720], and the low yields [P. Y. Maximov, D. J. Fernandes, R. E. McDaniel, C. B. Myers, R. F. Curpan and V. C. Jordan, *J. Med. Chem.,* 2014, 57, 4569]. In organic chemistry, chemistry of heterocyclic compounds is an interesting area of research since last decades. Various heteroatoms like oxygen [Liu, R. S. *PURE APPL CHEM.,* 2001, 73, 265-269], phosphorus [G. P. V. Reddy, Y. B. Kiran, S. C. Reddy and D. C. Reddy, *Chem. Pharm. Bull.,* 2004, 52, 307-310], sulfur, nitrogen [M. G. Valverde and T. Torroba, *Molecules.,* 2005, 10, 318-320] and selenium [A. Hafez, *Eur. J. Med. Chem.,* 2008, 43, 1971-1977] containing heterocycles are very attention grabbing. However, among them, N-containing heterocyclic compounds have maintained the interest of researchers through decades of historical development of organic synthesis. According to FDA database, the nitrogen-based heterocycles shows their structural significance in the drug design and engineering of pharmaceuticals, with nearly 60% of unique small-molecule drugs containing nitrogen heterocycles [E. Vitaku, D. T. Smith and J. T. Njardarson, *J. Med. Chem.,* 2014, 57, 10257-10274.]. Moreover, benzocycloheptene moieties contain fused six and seven membered ring system, their derivatives possess potential bacteriostatic, antipyretic, anti-inflammatory, anti-ulcer, CNS-stimulant, CNS-depressant and anti-convulsant activities [B. J. Crielaard, S. Van der Wal, T. Lammers, H. T. Le, W. E. Hennink, R. M. Schiffelers, G. Storm and M. H. A. M. Fens, *Int. J. Nanomed.,* 2011, 6, 2697-2703]. Some of the benzocyclohepta bicycle fused to nitrogen heterocycles derivatives present interesting pharmaceutical activities. Thus, 6,11-dihydro-5H-benzo[5,6]cyclohepta-[1,2-b]pyridine and N-substituted benzo[5,6]cyclohepta[1,2-b]indole are potent antitumor agents [A. Afonso, J. M. Kelly, J. Weinstein, R. L. Wolin, S. B. Rosenblum, U.S. Pat. No. 6,218,401. 2001, Chemical Abstract 134, 295746; J. Benoit, D. Alagille, J.-Y. Merour and S. Leonce, *Chem. Pharm. Bull.,* 2000, 48, 1872-1876] against L1210 murine leukemia and HT29 cell lines, while piperazinyl and piperidinyl derivatives inhibit the farnesyl protein transferase (FPT) [S. W. Remiszewski, R. J. Doll, C. Alvarez, T. Lalwani, U.S. Pat. No. 6,211,193, 2001. Chemical Abstract 134, 266206]. Synthesis of fused heterocyclic benzocycloheptene derivatives and efficiently execution these synthesized molecules into bioactive molecules is an attention grabbing topic in medicinal chemistry. Sulfones are valuable synthetic targets [M. N. Noshi, A. El-awa, E. Torres and P. L. Fuchs, *J. Am.* Chem. Soc., 2007, 129, 11242-11247; J. N. Desrosiers and A. B. Charette, *Angew Chem.* Int. Ed., 2007, 46, 5955-5957;. G. Pandey, K. N. Tiwari and V. G. Puranik, *Org. Lett.,* 2008, 10, 3611-3614; K. Oh. *Org. Lett.,* 2007, 9, 2973-2975] due to versatility of sulfone moieties [T. Nishimura, Y. Takiguchi and T. Hayashi, *J. Am. Chem. Soc.,* 2012, 134, 9086-9089; J. N. Desrosiers and W. S. Bechara, *Org. Lett.,* 2008, 10, 2315-2318]. It is a significant component in naturally occurring products and in drug discovery [U. Mahesh, K. Liu, R. C. Panicker and S. Q. Yao, *Chem. Commun.,* 2007, 1518-1520. J. J. Wang, X. Feng, Z. Xun, D. Q. Shi and Z. B. Huang, *J. Org. Chem.,* 2015, 80, 8435-42. Forristal, I. *J. Sulphur Chem.,* 2005, 26, 163. F. Hof, A. Schutz, C. Fah, S. Meyer, D. Bur, J. Liu, D. E. Goldberg, and E. Diederich, *Angew. Chem., Int. Ed.,* 2006, 45, 2138-2141]. The compounds containing sulfone group is very important in medicinal chemistry such as Rofecoxib, non-steroidal anti-inflammatory (NSAID) used in the treatment of arthritis and other similar conditions causing chronic or acute pain, Sulindac sulfone is used in the treatment of tumor and HCA-7 cells which leads to inhibition of prostaglandin E2 production [C. S. Williams, A. P. Goldman, H. Sheng, J. D. Morrow, and R. N. D. Bois, *Neoplasia.,* 1999, 1, 170-176] and Bicalutamide used in the treatment of prostate cancer [P. F. Schnellhammer, *Expert Opin. Pharmacother,* 2002, 3, 1313-1328]. Other sulfone derivatives have been used as drugs due to their high potential as antibacterial, antifungal, anti-nociceptive and anti-inflammatory agents such ad Lasix, Aquazide h, Sulfadimidine [K. Rais-Bahrami, M. Majd, E. Veszelovszky, and B. L. Short, *Am. J. Perinatol.,* 2004, 21, 329-332. J. D. Duarte, and R. M. Cooper-DeHoff, *Expert Rev Cardiovasc Ther.,* 2010, 8, 793-802. A. Romvary, and F. Simon, *Acta Vet Hung.,* 1992, 40, 99-106. W. Billard, H. Binch, K. Bratzler, L. -Y., Chen, G. C. Jr, R. A. Duffy, S. Dugar, J. Lachowicz, R., McQuade, P. Pushpavanam, V. B. Ruperto, L. A. Taylor, and J. W. Clader, *Bioorg. Med. Chem. Lett.* 2000, 10, 2209-2212. V. Padmavathi, P. Thriveni, G. S. Reddy, and D. Deepti, *Eur. J. Med. Chem.,* 2008, 43, 917-924. N. K. Konduru, S. Dey, M. Sajid, M. Owais, and N. Ahmed,. *Eur. J. Med. Chem.,* 2013 59, 23-30. P. A. Todd, and S. P. Clissold, Tenoxicam. *Drugs.,* 1991, 41, 625-646. C. R. Lee, and J. A. Balfour, (1994). Piroxicam-β Cyclodextrin. *Drugs.,* 1994, 48, 907-929.] well-known drugs in market Dapsone and Promine [G. H. Faget, R. C. Pogge, F. A. Johansen, J. F. Dinan, B. M. Prejean, and C. G. Eccles, *Int J Lepr Other Mycobact Dis.,* 1966, 34, 298-310.] The sulfone moiety also finds its value in the agrochemical field such as Mesotrione and Cafenstrole reported as herbicide [G. Mitchell, D. W. Bartlett, T. E. M. Fraser, T. R. Hawkes, D. C. Holt, J. K. Townson, and R. A. Wichert, *Pest Manag Sci.,* 2001, 57, 120-128. P. Boger. *J Pest Sci.,* 2003, 28, 324].

Background of PI3K and MK2:

The phosphoinositide 3-kinase (PI3K) is one of the most studied kinases, which plays pivotal role in regulation of various cellular processes and pathogenesis of Inflammation, Cancer and Diabetes. Kinases of PI3K family acts separately as well as in synergistic manner to regulate crucial signaling and metabolic processes. There is an augmented recognition of the key importance of three different PI3K classes (I, II and III) with their isoforms in various disease progression [S. Jean, and A. A. Kiger, 2014].

Due to their key crosstalk between themselves and kinases form other signaling pathways, class I PI3K isoforms have always been epicenter of the drug discovery as potent drug targets in the management of various diseases and helps in the quest of class-I-related therapies [A. Carracedo, and P. P. Pandolfi, *Oncogene.,* 2008, 27, 5527].

Role of PI3K:

Inflammation: Previous studies have found that class I PI3K isoforms have great significance in inflammation and immunomodulation [A. K. Stark, S. Sriskantharajah, E. M. Hessel, and K. Okkenhaug, *Current opinion in pharmacology,* 2015, 23, 82-91] [D. A. Fruman, and C. Rommel, *Nature reviews Drug discovery,* 2014, 13, 14]. Ubiquitous presence of PI3K-p110α is essential for angiogenesis and insulin signaling. PI3K-p110/120γ and PI3K-p110δ are mostly cell surface receptor dependent and are found in different immune cells like macrophages, dendritic cells, mast cell, T cells and B cell regulating growth and differentiations through signal transmissions.

Since numerous studies have established the fact that PI3K kinase is involved in key signalling and metabolic pathways of inflammation, rheumatoid arthritis and senescence, therefore, considering the facts that in diseases where pro-inflammatory cytokine response is dysregulated, PI3K kinases could be a promising therapeutic target.

Cancer: Numerous studies linked the phosphoinositide 3-kinase (PI3K) pathway with activation of receptor tyrosine kinases (RTKs), G protein-coupled receptors (GPCRs) and oncogenes such as RAS which ultimately affects various key cellular functions including cell proliferation, apoptosis and tumorigenesis. Along with it, comprehensive genome analysis of different human tumor samples have revealed the presence of mutations or alterations in components of PI3K signalling pathways [R. K. Thomas, A. C. Baker, R. M. DeBiasi, W. Winckler, T. LaFramboise, W. M. Lin, M. Wang, W. Feng, T. Zander, L. E. MacConaill, and J. C. Lee, *Nat Genet.,* 2007, 39, 347; Y. Samuels, Z. Wang, A. Bardelli, N. Silliman, J. Ptak, S. Szabo, H. Yan, A. Gazdar, S. M. Powell, G. J. Riggins, and J. K. Willson, *Science.,* 2004, 304, 554-554]. Inclusively, PI3K has been directly implicated in number of cancers including colon, brain, gastric, breast and lung cancer. [L. D. Wood, D. W. Parsons, S. Jones, J. Lin, T. Sjöblom, R. J. Leary, D. Shen, S. M. Boca, T. Barber, J. Ptak, and N. Silliman, *Science.,* 2007, 318, 1108-1113; R. K. Thomas, A. C. Baker, R. M. DeBiasi, W. Winckler, T. LaFramboise, W. M. Lin, M. Wang, W. Feng, T. Zander, L. E. MacConaill, and J. C. Lee, *Nat Genet.,* 2007, 39, 347; Cancer Genome Atlas Research Network, *Nature.,* 2008, 455, 1061; L. Ding, G. Getz, D. A. Wheeler, E. R. Mardis, M. D. McLellan, K. Cibulskis, C. Sougnez, H. Greulich, D. M. Muzny, M. B. Morgan, and L. Fulton, *Nature.,* 2008, 455, 1069; Y. Samuels, Z. Wang, A. Bardelli, N. Silliman, J. Ptak, S. Szabo, H. Yan, A. Gazdar, S. M. Powell, G. J. Riggins, and J. K. Willson, *Science.,* 2004, 304, 554-554; A. Di Cristofano, M, De Acetis, A. Koff, C. Cordon-Cardo, and P. P. Pandolfi, *Nat Genet.,* 2001, 27, 222;, D. W. Parsons, S. Jones, X. Zhang, J. C. H. Lin, R. J. Leary, P. Angenendt, P. Mankoo, H. Carter, I. M. Siu, G. L. Gallia, and A. Olivi, *Science.,* 2008, 321, 1807-1812; P. Liu, H. Cheng, T. M. Roberts, and J. J. Zhao, *Nat Rev Drug Discov.,* 2009, 8, 627].

Rheumatoid arthritis: Recent studies had shown that targeting PI3K isoforms in a mouse model of systemic lupus erythematosus can reduce glomerulonephritis and suppresses disease progression in rheumatoid arthritis mouse models [C. Rommel, M. Camps and, H. Ji, *Nature Reviews Immunology.,* 2007, 7, 191].

Lung fibrosis and Asthma: Regulation of inflammation and fibrosis has been shown to be governed by four class I PI3Ks [C. C. Campa, R. L. Silva, J. P. Margaria, T. Pirali, M. S. Mattos, L. R. Kraemer, D. C. Reis, G. Grosa, F. Copperi, E. M. Dalmarco, and R. C. Lima-Júnior,. *Nature communications.,* 2018, 9, 5232]. For example, a variety of leukocyte functions, including proliferation, differentiation, migration, and survival, are controlled by PI3Kγ and δ. Furthermore, proliferation of different lung cell types is governed by PI3Kα and β, PI3Kγ and β has been found involved in pulmonary inflammation and fibrotic remodelling which ultimately leads to lung fibrosis and asthma. [P. T. Hawkins, and L. R. Stephens, PI3K signalling in inflammation, *Biochimica et Biophysica Acta* (BBA)-Molecular and Cell Biology of Lipids, 2015, 1851, 882-897; A. Ghigo, F. Damilano, L. E. Bioessays, 32, 185-196, R. C. E. Roffe, A. L. Souza, L. P. Sousa, M. Mirolo, A. Doni, and G. D, *J. Leukoc. Biol.,* 2011, 89, 269-282]. Diabetes related disorders: PI3K regulates glucose uptake in the cells by downstream activation of AKT and hexokinase. Increase in glucose uptake is the immediate effect of insulin driven PI3K signalling in muscle and fat cells, attributable to increased glucose translocation to the membrane and upregulation of the genes encoding the transporters [[L. C. Cantley, and Z. Songyang, *J Cell Sci,* 1994, 121-126]. Receptor tyrosine kinases undergo conformational changes after stimulation of the growth factor, allowing them to auto-phosphorylate and become active. Subsequently, AKT2 is phosphorylated and inhibits RabGAP and AS160, resulting into migration of glucose transporter GLUT4 to the plasma membrane [J. Yuasa-Kawada, M. Kinoshita-Kawada, Y. Rao, and J. Y. Wu, Proceedings of the National Academy of Sciences, 2009, 106, 14530-14535; L. C. Cantley,. *Science,* 2002, 296, 1655-1657]

Mapkapk2

MAPKPAK2 or, MK2 is downstream substrate of p-38 MAPK in MAPK pathway and have been found to be extremely involved in oxidative stress, inflammation, regulation of cell cycle, tumorigenesis and cell migration [Gurgis, Fadi Maged Shokry, William Ziaziaris, and Lenka Munoz, *Mol Pharmacol.,* 2014, 345-356; Maruyama, Junichi, et al. *Curr Med Chem.,* 2009, 1229-1235; Jackson, Robert M., and Rolando Garcia-Rojas, *Exp Lung Res.,* 2008, 245-262]. Key studies elucidated its role at post transcriptional level in gene expression, cell proliferation and apoptosis through modulation of transcript stability via RBPs (RNA Binding Proteins) [Pearson, Gray, et al. *Endocr Rev.,* 2001, 153-183; S. Soni, P. Anand, and Y. S. Padwad, *J Exp Clin Cancer Res.,* 2019, 38, 121; S. Soni, M. K. Saroch, B. Chander, N. V. Tirpude, and Y. S. Padwad, *J Exp Clin Cancer Res.,* 2019, 38, 175]. Furthermore, MK2 has been found to regulate various cellular processes in response to extracellular signals including oxidative stress, inflammation, infection, radiation and genotoxicity [S. J. Diaz-Cano, Re. Pomerance et al. *J. Pathol.,* 2006, 209, 298-306*; J. Pathol.,* 2006, 210, 133, A. Kotlyarov, Y. Yannoni, S. Fritz, K. LaaB, J. B. Telliez, D. Pitman, L. L. Lin and M. Gaestel, *Mol Cellular Biol.* 2002, 22, 4827-35].

Upon activation from p38-MAPK, cytoplasmic localization of MK2 takes place with the help of nuclear export signals (NES) [Pearson, Gray, et al. Endocrine reviews, 2001, 153-183;, S. Soni, P. Anand, and Y. S. Padwad, *Journal of Experimental & Clinical Cancer Research.,* 2019, 38, 121,; S. J. Diaz-Cano, Re. Pomerance et al. *J. Pathol,* 2006, 209, 298-306. *J. Pathol.,* 2006, 210, 133], where it directly acts upon its crucial downstream substrates like Hsp27 (Heat Shock protein 27) and leads to remodeling of cellular cytoskeleton, cell migration, cell invasion and metastasis [F. M. Gurgis, W, Ziaziaris and L. Munoz, *Mol Pharmacol.* 2014, 85, 345-356, Rogalla, Thorsten, et al. *J Biol Chem.,* 1999, 18947-18956].]. Additionally, MK2 favors the cell survival by reversing post chemotherapy DNA damage through activating G2/M arrest via checkpoint signaling, ultimately imposing resistance to the therapeutic protocol [Cannell, Ian G., et al. *Cancer cell.,* 2015, 623-637].

Role of MK2:

Inflammation: MK2 extensively regulates the biosynthesis of TNFα and production of pro-inflammatory mediators like TNFα, IL-1, IL-β, IL-6, interferon-γ (IFNγ) and other cytokines [Rogalla, Thorsten, et al. *J Biol Chem.,* 1999, 18947-18956]. MK2 proved to be essential for the stimulation of cytokine biosynthesis through LPS-induced upregulation of cytokine mRNA stability and translation. This is supported by a substantial reduction in TNFα synthesis despite of LPS induction in MK2 deficient transgenic mice model [R. Winzen, M. Kracht, B. Ritter, A. Wilhelm, C. Y. A. Chen, A. B. Shyu, M. Müller, M. Gaestel, K. Resch, and H. Holtmann, *The EMBO journal.,* 1999, 18, 4969-4980; Rogalla, Thorsten, et al. *J Biol Chem.,* 1999, 18947-18956]. MK2 has also been implicated in RIPK1 inhibition by limiting its cytotoxic and apoptotic activity, hence, increase cytokine expression during inflammation [M. B. Menon, J. GropengieBer, J. Fischer, L. Novikova, A. Deuretzbacher, J. Lafera, H. Schimmeck, N. Czymmeck, N. Ronkina, A. Kotlyarov, and M. Aepfelbacher, *Nat Cell Biol.,* 2017, 19, 1248].

Cancer: A vast array of studies has been reported direct role of MK2 in cell cycle regulation, modulation of RBPs, uncontrolled cell proliferation, tumorigenesis and metastasis. In the events of cell cycle, MK2 phosphorylates CDC25 family members (CDC25B and CDC25C) to persuade 14-3-3 binding which leads to the arrest of cell cycle [I. A. Manke, A. Nguyen, D. Lim, M. Q. Stewart, A. E. Elia, and M. B. Yaffe, *Mol Cell.,* 2005, 17, 37-48]. MK2 also targets the activation of ubiquitin ligase HDM2 to promote degradation of p53 leading to post DNA damage cell survival [H. O. Weber, R. L. Ludwig, D. Morrison, A. Kotlyarov, M. Gaestel, and K. H. Vousden, *Oncogene.,* 2005, 24, 1965] and has also been linked with imposing resistance to the apoptosis caused by p53 mutation [F. M. Gurgis, W, Ziaziaris and L. Munoz, *Mol Pharmacol.* 2014, 85, 345-56].

Additionally, MK2 plays role in Mdm2 activation, resulting into Mdm2 mediated p53 inactivation and degradation, confirmed by rise in p53 level in $MK^{-/-}$ cells in contrast to low Mdm2 levels [H. O. Weber, R. L. Ludwig, D. Morrison, A. Kotlyarov, M. Gaestel, and K. H. Vousden, *Oncogene.,* 2005, 24, 1965]. These studies have established MK2 as a DNA damage checkpoint kinase functioning parallel to conventional CHK1 and CHK2 [Cannell, Ian G., et al. *Cancer cell.,* 2015, 623-637, I. A. Manke, A. Nguyen, D. Lim, M. Q. Stewart, A. E. Elia, and M. B. Yaffe, Molecular cell, 2005, 17, 37-48, M. B. Menon, J. GropengieBer, J. Fischer, L. Novikova, A. Deuretzbacher, J. Lafera, H. Schimmeck, N. Czymmeck, N. Ronkina, A. Kotlyarov, and M. Aepfelbacher, *Nat Cell Biol.,* 2017 19, 1248]. MK2 orchestrate mRNA stability of genes as well as phosphorylation and expression of numbers of proteins involved in immune response [J. S. Erdem, V. Skaug, A. Haugen and S. Zienolddiny, *J Cancer.,* 2016, 7, 512], cell cycle [[F. M. Gurgis, W, Ziaziaris and L. Munoz, *Mol Pharmacol.* 2014, 85, 345-56.], cytoskeleton remodelling [Rogalla, Thorsten, et al. *J Biol Chem.,* 1999, 18947-18956; A. Kotlyarov, Y. Yannoni, S. Fritz, K. LaaB, J. B. Telliez, D. Pitman, L. L. Lin and M. Gaestel, *Mol Cellular Biol.,* 2002, 22, 4827-35.50; 51. B. Kumar, S. Koul, J. Petersen, L. Khandrika, J. S. Hwa, R. B. Meacham, S. Wilson and H. K. Koul, *Cancer Res.,* 2010, 70, 832-41.51], evasion of apoptosis and cell migration [Rogalla, Thorsten, et al. *J Biol Chem.,* 1999, 18947-18956 40; F. M. Gurgis, W, Ziaziaris and L. Munoz, *Mol Pharmacol.* 2014, 85, 345-56; B. Kumar, S. Koul, J. Petersen, L. Khandrika, J. S. Hwa, R. B. Meacham, S. Wilson and H. K. Koul, *Cancer Res.,* 2010, 70, 832-41.] in response to external stimuli. These stimuli are abundant in tumor microenvironment and most of the time initiate the activation of MK2 and subsequently its downstream substrates like Hsp27, modulating the levels of cytokines, chemokines and matrix metalloproteinases (MMPs), finally resulting into facilitation of tumor microenvironment, neoangiogenesis and extravasation.

Various key studies performed in the area specifically support the direct involvement of MK2 and its downstream substrate Hsp27 in the pathogenesis of different cancers, prominently including intestinal cancer [A. Henriques, V. Koliaraki, G. Kollias, and Mesenchymal, *Proc Natl Acad Sci*., USA. 2018, 115, E5546-55,; H. R. Cheruku., A. Mohamedali, D. I. Cantor, S. H. Tan, E. C. M. S. Nice. *EuPA Open Proteom.,* 2015, 8, 104-15.], skin cancer [C. Johansen, C. Vestergaard, K. Kragballe, G. Kollias, M. Gaestel, and L. Iversen, *Carcinogenesis.,* 2009, 30, 2100-8], bladder cancer [B. Kumar, J. Sinclair, L. Khandrika, S. Koul, S. Wilson and H. K. Koul, *Int J Oncol.,* 2009, 34, 1557-64.], prostate cancer [S. A. Hayes, X. Huang, S. Kambhampati, L. C. Platanias and R. C. Bergan, *Oncogene.,* 2003, 22, 4841.], lung cancer [B. Liu, L. Yang, B. Huang, M. Cheng, H. Wang, Y. Li, D. Huang, J. Zheng, Q. Li, X. Zhang, and W. Ji, *Am J Hum Genet.,* 2012, 91, 384-390, J. S. Erdem, V. Skaug, A. Haugen, and S. Zienolddiny, *J. Cancer.,* 2016, 7, 512] and head and neck cancer [S. Soni, M. K. Saroch, B. Chander, N. V. Tirpude, and Y. S. Padwad, *J Exp Clin Cancer Res.* 2019, 38, 17535].

Alzheimer's disease and Neuroinflammation: Current evidences supports the role of MK2 in regulation of various inflammatory cytokines expressions in neuroinflammation-associated important brain disorders. For example, MK2 was found to be overexpressed in $LPS^{+}$ IFF-gamma stimulated microglial cells. Ex-vivo cultured microglia from MK2 $^{(-/-)}$ mice have shown significant inhibition in the release of TNFα and MIP-1α (macrophage inflammatory protein-1α) as compared to $MK2^{(+/+)}$ wild-type microglia. In addition to this, deficiency of MK2 in APP-PS1 transgenic Alzheimer mouse promotes autophagy/macroautophagy. Based on the evidences from various studies, it is clear that MK2 contributes to the pathophysiology of Alzheimer's disease and Parkinson's disease [F. M. Gurgis, W, Ziaziaris and L. Munoz, *Mol Pharmacol.* 2014, 85, 345-56, A. A. Culbert, S. D. Skaper, D. R. Howlett, N. A. Evans, L. Facci, P. E. Soden, Z. M. Seymour, F. Guillot, M. Gaestel, and J. C. Richardson, *J Biol Chem.,* 2006, 281, 23658-23667, S. A. Correa, and K. L. Eales, *Journal of signal transduction.,* 2012, *J. Alam, and W. Scheper, Autophagy.,* 2016, 12, 2516-2520.].

Lung injury and pulmonary fibrosis: MK2 has been long implicated in the inflammation via activation of NADPH oxidase, regulation of TNF-α levels, neutrophil recruitment and cell cycle arrest. These mechanisms have been found to be involved in the molecular pathogenesis of acute lung injury, pulmonary fibrosis, and non-small-cell lung cancer [F. Qian, J. Deng, G., Wang, D Ye, R. and W Christman, *Curr Protein Pept Sci.,* 2016, 17, 332-342]. Increase in MK2 mediated inflammatory cytokines mRNAs results in actin reorganization, change in cell adhesion properties, increase in α-SMA (α-smooth muscle actin) protein expression and myofibroblast differentiation. Combinatory, all these events lead to regulation of cytoskeleton structure and facilitates lung injury and pulmonary fibrosis [L. B. Lopes, E. J. Furnish, P. Komalavilas, C. R Flynn, P. Ashby, A. Hansen, D. P. Ly, G. P. Yang, M. T. Longaker, A. Panitch, and C. M. Brophy, *J Invest Dermatol.,* 2009, 129, 590-598.61; R. K. Singh and A. K. Najmi, *Curr Drug Targets.,* 2019, 20, 367-379, R. Vittal, A. Fisher, H. Gu, E. A. Mickler, A. Panitch, C. Lander, O. W. Cummings, G. E. Sandusky, and D. S. Wilkes, *Am J Respir Cell Mol Biol.,* 2013, 49, 47-57.].

Asthma: It has been observed in the studies that, MK2 is necessary to produce localized Th2-type inflammation and subsequently develops experimental asthma. Although MK2 doesn't affect systemic Th2 immunity, but it reduces expression of chemokines, adhesion molecules and also decreases endothelial permeability. Additionally, transcriptional expression of chemokines and adhesion molecules have been found to associate with NF-κB and it is well versed that MK2 and its downstream Hsp27 are essential for sustained production of NF-κB [M. M. Gorska, Q. Liang, S. J. Stafford, N. Goplen, N. Dharajiya, L. Guo, S. Sur, M. Gaestel, and R. Alam, *J. Exp. Med.,* 2007, 204, 1637-1652].

Rheumatoid arthritis: TNF-alpha has been shown to play an important role in Rheumatoid arthritis (RA) by mediating immune regulation and inflammatory response. MK2 has been long associated with biosynthesis of TNF-alpha at a posttranscriptional level, so the studies based on this supports the direct involvement of MK2 in RA. This has been confirmed in the DBA/1Lacj collagen-induced arthritis (CIA) mice model by deletion of the MK2 gene, which enhanced protection against CIA [M. Hegen, M. Gaestel, C. L. Nickerson-Nutter, L. L. Lin, and J. B. Telliez, *J. Immunol.,* 2006, 177, 1913-1917].

Atherosclerosis: Study has been reported the functional role of MK2 and atherogenesis in hypercholesterolemia. Activated form of MK2 has been detected in endothelium and macrophage-rich plaque areas inside aortas of hypercholesterolemic LDL receptor deficient mice. Contrary, deletion of MK2 in hypercholesterolemic 1dlr(−/−) mice (1dlr(−/−)/mk2(−/−)) decreases the accumulation of lipid and macrophages in the aorta despite of an artherogenic diet and increased plasma lipoprotein levels [K. Jagavelu, U. J. Tietge, M. Gaestel, H. Drexler, B. Schieffer, and U. Bavendiek, *Circ Res.,* 2007, 101, 1104-1112].

Therefore, there is a need in the art for novel compounds for treatment of PI3K and MK2 related disorders.

Objectives of the Invention

The main objective of the present invention is to provide sulfonamide fused benzocycloheptenes of general formula I useful for treatment of diseases responsible through PI3K and MK2 pathway.

Yet another objective of the present invention is to provide furan and pyrrol substituted benzocycloheptenes of general formula II useful as PI3K and MK2 inhibitor for treatment of diseases.

Still another objective of the present invention is to provide alkyl carbonyl substituted benzocycloheptenes of general formula III useful as PI3K and MK2 inhibitor, for treatment of diseases.

Yet another objective of the present invention is to provide multi-ring fused quinolinone and quinolinol substituted benzocycloheptenes of general formula IV and V useful as PI3K and MK2 inhibitor, for treatment of diseases.

Still another objective of the present invention is to provide sulfone substituted benxocycloheptenes of general formula VI useful as PI3K and MK2 inhibitor, for treatment of diseases.

Yet another objective of the present invention is to provide a method for preparation of benzocycloheptene analogues of formula I-VI from himachalenes collected from *Cedrus deodara* oil.

SUMMARY OF THE INVENTION

As aspect of present invention provides a compound of general formula I, II, III, IV, V or VI:

I

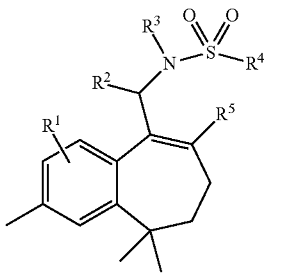

II

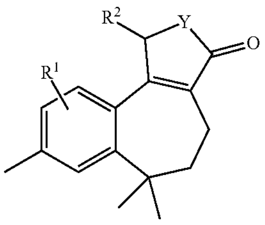

III

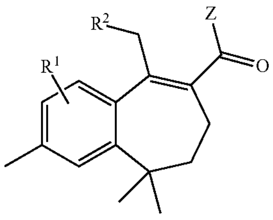

IV

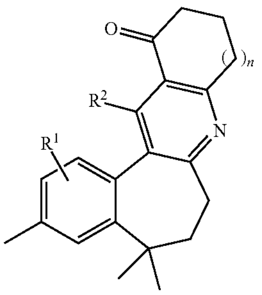

V

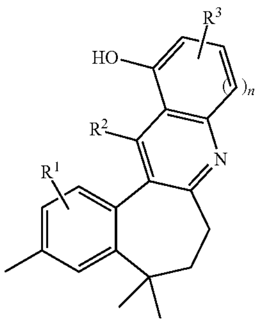

-continued

VI

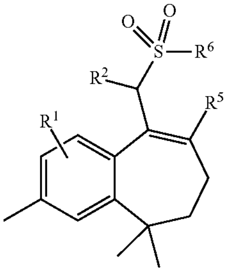

and pharmaceutical acceptable salts and enantiomers thereof, wherein Y is selected from the group consisting of C, O, N and S;

Z is selected from the group consisting of H, C1-C6 alkyl, C1-C6 aryl, halogen, oxygen, nitrogen and sulfur;

$R^1$ is selected from the group consisting of hydrogen, hydroxyl, nitrogen substituted group selected from benzylamine or aniline, S-containing group selected from thiophene, carboxylic acid and its derivatives selected from propanoic acid, and halogen;

$R^2$ is selected from the group consisting of H, C1-C6 alkyl, C1-C6 aryl, halide, C1-C6 amines and C1-C6 carbonyl group;

$R^3$ is selected from the group consisting of H, C1-C6 alkyl, C1-C6 aryl and sulfur containing group selected from thiophene;

X is selected from the group consisting of carbon, nitrogen, oxygen and sulfur;

$R^4$ is selected from the group consisting of H, C1-C6 alkyl, C1-C6 aryl, halogen and carbonyl group selected from aldehyde substituted benzenesulphonamide;

$R^5$ is selected from the group consisting of H, C1-C6 alkyl, C1-C6 aryl, halogen and C1-C6 carbonyl group;

$R^6$ is selected from the group consisting of H, C1-C6 alkyl, C1-C6 aryl and C1-C6 amine group.

Another aspect of the present invention provides a compound of formula I-VI for use as anti-type 2 diabetes, antipyretic, anti-inflammatory, anticancer, antiulcer, CNS-stimulant, and CNS-depressant.

Yet another aspect of the present invention provides a pharmaceutical formulation comprising the compound of formula I-VI along with a pharmaceutically acceptable adjuvant, diluent or carrier.

Still another aspect of the present invention provides a compound of formula I-VI, for use as an inhibitor of PI3K and MK2 mediated activity.

DETAILED DESCRIPTION OF THE INVENTION

Figure 1:
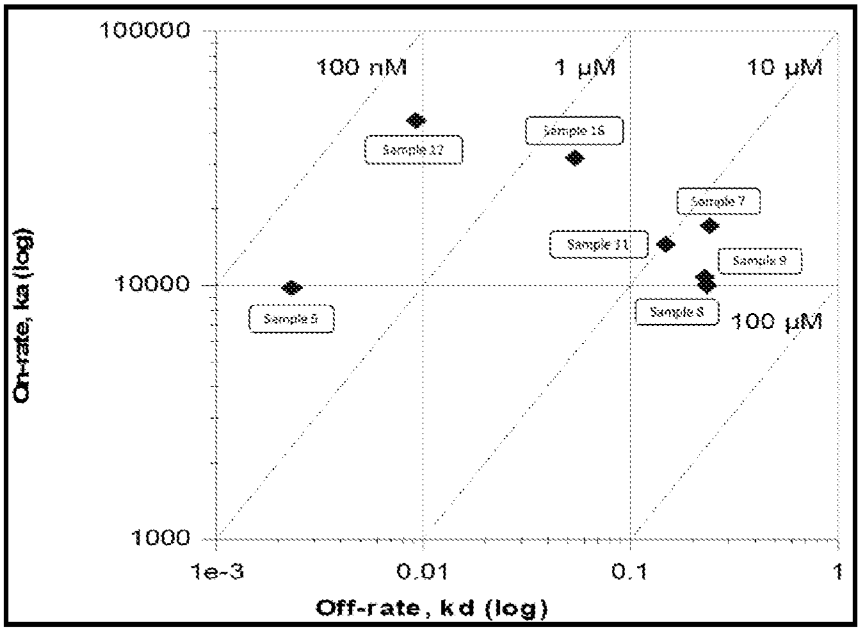
FIG. 1: Image depicts the on-rate and off-rate of binding of evaluated compounds of general formula II to PI3K (120y). Plotting association rate constant ka against dissociation rate constant kd (here on logarithmic scales) creates a plot where the affinity is represented by diagonal lines. Compounds on the same diagonal have the same affinity but differ in kinetics.

The present invention is directed towards substituted benzocycloheptene analogues, of general formula I, II, III, IV, V or VI General Formula I-VI

I

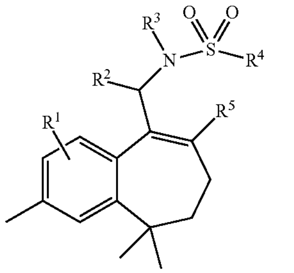

II

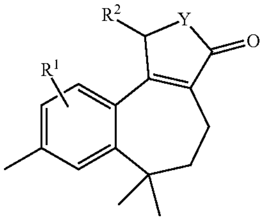

III

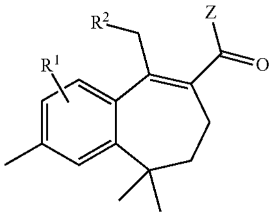

IV

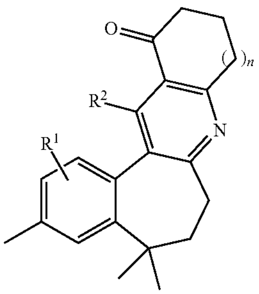

-continued

V

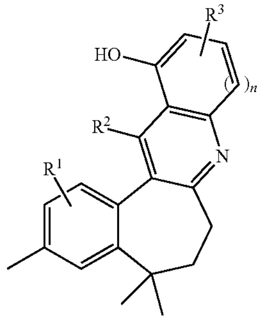

VI

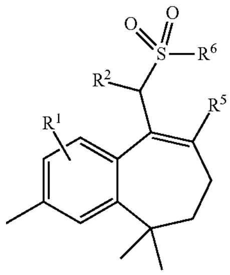

wherein in Formula I-VI, $R^1$ is selected from the group consisting of H, OH, N substituted group selected from benzylamine or aniline, S-containing group selected from thiophene, carboxylic acid and its derivatives selected from propanoic acid, and halogen;

$R^2$ is selected from the group consisting of H, C1-C6 alkyl, C1-C6 aryl, halide, C1-C6 amine and C1-C6 carbonyl group;

in Formula I, $R^3$—$R^5$ are each independently selected from the group consisting of H, C1-C6 alkyl, C1-C6 aryl, halogen and C1-C6 carbonyl group;

in Formula II, Y is selected from the group consisting of C, O, N and S;

in Formula III, Z is selected from the group consisting of H, C1-C6 alkyl, C1-C6 aryl, halogen, oxygen, nitrogen and sulfur;

in Formula IV, n varies from 5 to 6;

in Formula V, n varies from 5 to 6 and $R^3$ is selected from the group consisting of H, OH, N substituted group selected from pyridine, carboxylic acid and its derivatives selected from propanoic acid and halogen;

in Formula VI, $R^5$ is selected from the group consisting of H, halide, oxygen, nitrogen containing group selected from the group consisting of enaminone, cyclohexane 1,3-dione, C1-C6 alkyl and C1-C6 aryl group; and $R^6$ is selected from the group consisting of C1-C6 alkyl, C1-C6 aryl, hydrogen and hetero atoms selected from thiophene.

The present invention provides a compound of general formula I, II, III, IV, V or VI:

I

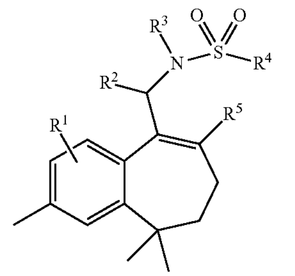

II

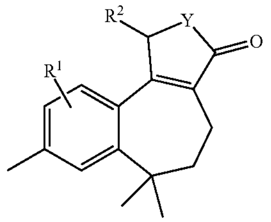

III

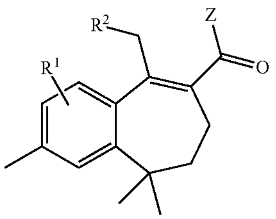

IV

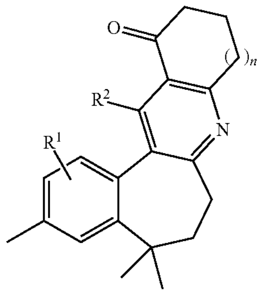

V

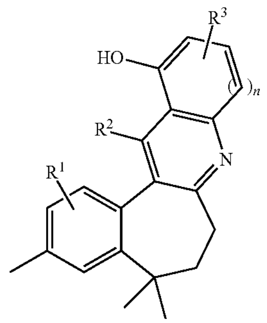

-continued

VI

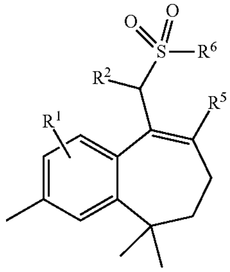

and pharmaceutical acceptable salts and enantiomers thereof, wherein

Y is selected from the group consisting of C, O, N and S;

Z is selected from the group consisting of H, C1-C6 alkyl, C1-C6 aryl, halogen, oxygen, nitrogen and sulfur;

$R^1$ is selected from the group consisting of hydrogen, hydroxyl, nitrogen substituted group selected from benzylamine or aniline, S-containing groups selected from thiophene, carboxylic acid and its derivatives selected from propanoic acid, and halogen;

$R^2$ is selected from the group consisting of H, C1-C6 alkyl, C1-C6 aryl, halide, C1-C6 amine and C1-C6 carbonyl groups;

$R^3$ is selected from the group consisting of H, C1-C6 alkyl, C1-C6 aryl and sulfur containing group selected from thiophene;

X is selected from the group consisting of carbon, nitrogen, oxygen and sulfur;

$R^4$ is selected from the group consisting of H, C1-C6 alkyl, C1-C6 aryl, halogen and carbonyl group selected from aldehyde substituted benzenesulphonamide;

$R^5$ is selected from the group consisting of H, C1-C6 alkyl, C1-C6 aryl, halogen and C1-C6 carbonyl group; and $R^6$ is selected from the group consisting of H, C1-C6 alkyl, C1-C6 aryl and C1-C6 amine group.

In an embodiment of the present invention there is provided a compound of the formula (I), wherein $R^1$ is selected from the group consisting of H, OH, N substituted group selected from benzylamine or aniline, carboxylic acid and its derivatives selected from propanoic acid and halogens, $R^2$ is selected from the group consisting of H, C1-C6 alkyl, C1-C6 aryl, halide, C1-C6 amine and C1-C6 carbonyl group; and $R^3$-$R^5$ are each independently selected from the group consisting of H, C1-C6 alkyl, C1-C6 aryl, halogen and C1-C6 carbonyl group.

In another embodiment of the present invention there is provided a compound of the formula (II), wherein $R^1$ is selected from the group consisting of H, OH, N substituted group selected from benzylamine, or aniline, carboxylic acid and its derivatives selected from propanoic acid, and halogen, $R^2$ is selected from the group consisting of H, C1-C6 alkyl, C1-C6 aryl, halide, C1-C6 amine and C1-C6 carbonyl group; and and Y is selected from the group consisting of C, O, N and S.

In yet another embodiment of the present invention there is provided a compound of the formula (III), wherein $R^1$ is selected from the group consisting of H, OH, N substituted group selected from benzylamine or aniline, carboxylic acid and its derivatives selected from propanoic acid, and halogen, $R^2$ is selected from the group consisting of H, C1-C6 alkyl, C1-C6 aryl, halide, C1-C6 amine and C1-C6 carbonyl group; and Z is selected from the group consisting of H, C1-C6 alkyl, C1-C6 aryl, halogen, oxygen, nitrogen and sulfur group.

In still another embodiment of the present invention there is provided a compound of the formula (IV), wherein $R^1$ is selected from the group consisting of H, OH, N substituted group selected from benzylamine, or aniline, carboxylic acid and its derivatives selected from propanoic acid and halogen, $R^2$ is selected from the group consisting of H, C1-C6 alkyl, C1-C6 aryl, halide, C1-C6 amine, and C1-C6 carbonyl group; and and n varies from 5 to 6.

In another embodiment of the present invention there is provided a compound of the formula (V), wherein $R^1$ is selected from the group consisting of H, OH, N substituted group selected from benzylamine or aniline, carboxylic acid and its derivative selected from propanoic acid and halogen, $R^2$ is selected from the group consisting of H, C1-C6 alkyl, C1-C6 aryl, halide, C1-C6 amine, and C1-C6 carbonyl group;

n varies from 5 to 6; and $R^3$ is selected from the group consisting of H, CJ-C6 alkyl, CJ-C6 aryl and halogen group.

In yet another embodiment of the present invention there is provided a compound of the formula (VI), wherein $R^1$ is selected from the group consisting of H, OH, N substituted group selected from benzylamine, or aniline, carboxylic acid and its derivatives selected from propanoic acid and halogen;

$R^2$ is selected from the group consisting of H, CJ-C6 alkyl, CJ-C6 aryl, halide, CJ-C6 amine and CJ-C6 carbonyl group;

$R^5$ is selected from the group consisting of hydrogen, CJ-C6 alkyl, halide, sulphur, C1-C6 amine and CJ-C6 aryl group; and $R^6$ is selected from the group consisting of H, C1-C6 alkyl, C1-C6 aryl and C1-C6 amine group.

In still another embodiment of the present invention there is provided a compound of the formula I-VI, for use as anti-type 2 diabetes, antipyretic, anti-inflammatory, anticancer, antiulcer, CNS-stimulant, and CNS-depressant.

Another embodiment of the present invention provides a pharmaceutical formulation comprising the compound of formula I-VI along with a pharmaceutically acceptable adjuvant, diluent or carrier.

In yet another embodiment of the present invention there is provided a compound of the formula I-VI, for use as an inhibitor of PI3K and MK2 mediated activity.

These substituted benzocycloheptene analogues are semi-synthesized from himachalenes extracted from *Cedrus deodara* oil.

The present invention discloses synthesis of benzocycloheptene compounds using easily available and low cost natural precursors i.e. *Cedrus deodara* oil following less steps, economic and cost-effective approach.

Under this investigation, semi-synthetic approaches have been developed to minimize number of challenging steps in organic synthesis and avoiding high cost reagents and chemicals to reduce overall cost of production.

Under this investigation, different new methodologies have been developed to overcome the existing challenges in this type of organic synthesis. High purity of the molecules (>98-99%) has been achieved through column chromatography.

The process is easy to apply for scale-up synthesis which is a very important issue to evaluate biological activities and future industrial interest.

These class of compounds are known for different biological activities therefore, facile approaches have been developed for different new classes of benzocycloheptene analogues synthesis following new process and further applied for treatment of PI3K and MK2 related disorders.

Further, the use of natural analogues also reduces the toxic effect and its specific structure enhances the chance of biological activities for therapeutic development.

Compounds constituted of complex bicyclic framework with alkyl group are difficult to introduce. Thus, the core structure is derived from natural precursor which reduces the cost of production, reagents and overall makes the process economic.

Compounds constituted from natural precursor are less toxic in nature and indicated different applications for treatment of PI3K and MK2 related disorders responsible for different diseases.

EXAMPLES

The following examples are given by way of illustration and therefore should not construed to limit the scope of the present invention.

Experimental Part

All reagents and solvents were purchased from commercial sources (Sigma-Aldrich, Merck India Ltd). Reactions were monitored by TLC plates coated with 0.2 mm silica gel 60 $F_{254}$. TLC plates were visualized by UV irradiation (254 nm) and iodine spray. The products were purified by column chromatography employing silica gel of 60-120 mesh size (Merck). The $^1$H and $^{13}$C NMR spectra were recorded at 298 K with a Bruker AM-300 spectrometer; using TMS as internal reference standard in $CDCl_3$. HRMS were conducted with UHR-QTOF (ultra-high resolution Q-time of flight). IR spectra were obtained on a Nicolet 5700 FTIR (Thermo, USA) spectrophotometer in the region 4,000-400 cm-1 using KBr disks. CEM Discover™ focused microwaves (2450 MHz, 300 W) were used. The temperature on the surface of the reaction flask was measured with an inbuilt infrared temperature probe in the microwave experiment. The coupling constants (J) are reported in hertz (Hz) and the following abbreviations are used to designate signal multiplicity: s=singlet; d=doublet; t=triplet; m=multiplet; br=broad singlet.

Example 1

General Procedure for the Synthesis of Formula I

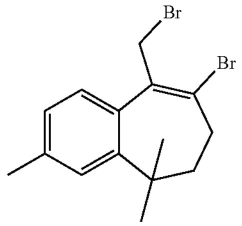

+

-continued

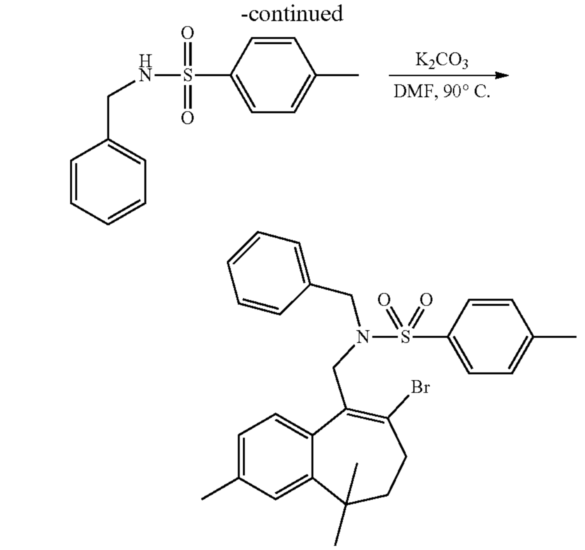

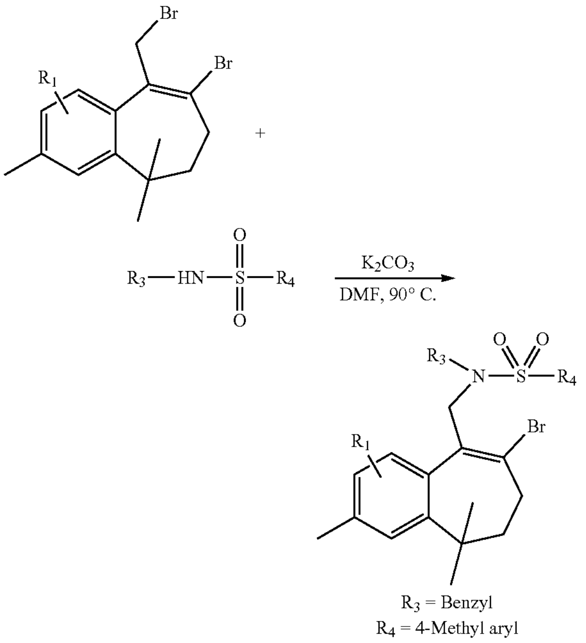

Synthesis of N-benzyl-N-((8-bromo-3,5,5-trimethyl-6,7-dihydro-5H-benzo[7] annulen-9-yl)methyl)-4-methylbenzenesulfonamide A mixture of 8-bromo-9-(bromomethyl)-3,5,5-trimethyl-6,7-dihydro-5H-benzo[7]annulene (0.279 mmol, 1.0 equiv.), N-benzyl-4-methylbenzzenesulfonamide (0.41 mmol, 1.5 equiv.), $K_2CO_3$ (0.55 mmol, 2 equvi.) in DMF (3 ml) were placed in reaction tube (15 mL) at 90° C. for 16 h. After cooling the reaction mixture to ambient temperature, water was added and extracted with ethyl acetate (10x3 times). The combined organic layer was washed with water and dried over $Na_2SO_4$ and vacuum evaporated. The viscous liquid obtained was purified by column chromatography on silica gel (mesh 60-120) using the mixture of hexane: EtOAc (80:20) to obtain the desired product as yellow oily (45 mg, 30%).

$^1H$ NMR ($CDCl_3$, 300 MHz, δ, ppm): 1.08 (s, 6H), 1.94-1.89 (m, 2H), 2.32-2.24 (m, 8H), 4.33 (s, 2H), 4.36 (s, 2H), 6.96-6.94 (d, J=7.8, 1H), 7.08-7.05 (d, 3H), 7.21-7.11 (m, 5H), 7.36-7.29 (m, 3H); $^{13}C$ NMR ($CDCl_3$, 75 MHz) δ, 21.4, 21.5, 31.6, 37.6, 38.6, 47.3, 51.8, 52.6, 126.6, 126.6, 127.2, 127.3, 128.1, 129.0, 133.3, 134.5, 136.4, 136.9, 137.1, 142.8, 146.2. ESI-MS: calcd for $C_{29}H_{32}BrNO_2S$ $[M+H]^+$ 538.1410, found 538.0189.

Example 2

General Procedure for the Synthesis of Formula II

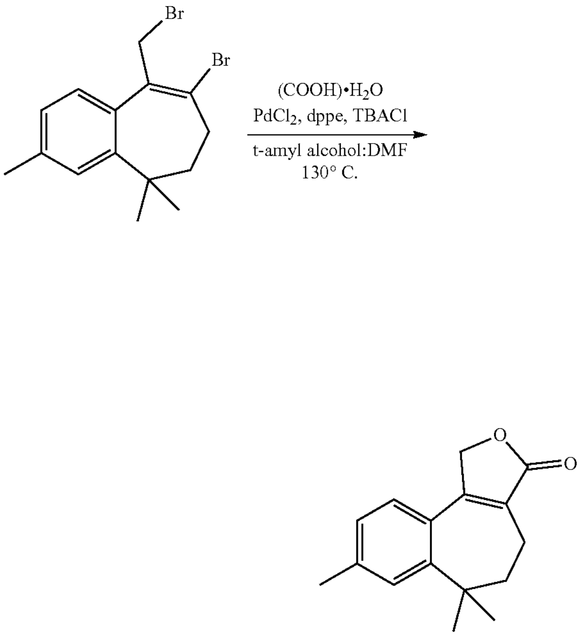

Synthesis of 6,6,8-trimethyl-1,4,5,6-tetrahydro-3H-benzo[3,4]cycloheptal[1,2-c]furan-3-one A mixture of 8-bromo-9-(bromomethyl)-3,5,5-trimethyl-6,7-dihydro-5H-benzo[7]annulene (0.279 mmol, 1.0 equiv.), oxalic acid (1.67 mmol, 6 equiv.), PdCl2 (0.013 mmol, 0.05 equiv.), dppe (0.013 mmol, 0.05 equiv.), TBACl (0.139 mmol, 0.50 equiv.) in DMF and t-amyl alcohol in 1:1 ratio (0.5:0.5 ml) was placed in a pressurized reaction tube (5 ml) under conventional heating (130° C.) for 20 hrs. After cooling to ambient temperature, water was added to the reaction mixture and extracted with ethyl acetate (3x10 ml). The combined organic layer was washed with water and dried over $Na_2SO_4$ and solvent was removed under reduced pressure. The viscous liquid obtained was purified by column chromatography on silica gel (60-120 mesh) using hexane:EtOAc (90:10) to afford the desired product as a white solid (97 mg, 40%).

$^1H$ NMR ($CDCl_3$, 300 MHz, δ, ppm):1.35 (s, 6H), 2.15-2.11 (m, 2H), 2.37 (s, 3H), 2.51-2.47 (t, 3H), 4.63 (s, 2H), 7.11-7.08 (d, J=6.99 Hz, 1H), 7.23 (s, 1H), 7.33-7.30 (d, J=7.86 Hz, 1H); $^{13}C$ NMR ($CDCl_3$, 75 MHz, δ, ppm): 20.1, 22.2, 27.5, 34.2, 36.6, 69.2, 125.1, 125.5, 125.7, 125.9, 139.1, 150.2, 151.6, 173.6. ESI-MS: calcd for $C_{16}H_{18}O_2$ $[M+H]^+$ 243.1380, found 243.3711.

Example 3

General Procedure for the Synthesis of Formula II

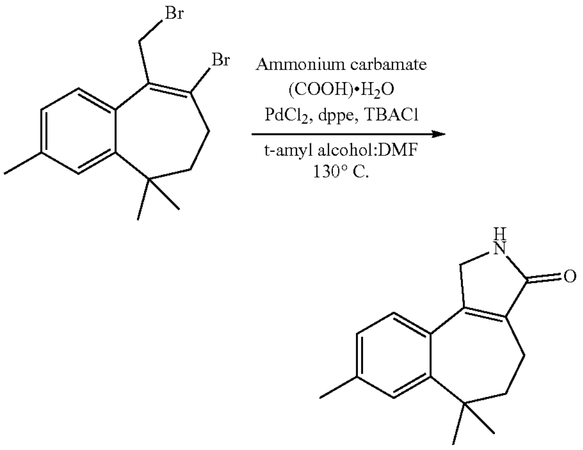

Formula II (a)

Synthesis of 6,6,8-trimethyl-1,4,5,6-tetrahydrobenzo[3,4]cyclohepta[1,2-c]pyrrol-3(2H)-one A mixture of 8-bromo-9-(bromomethyl)-3,5,5-trimethyl-6,7-dihydro-5H-benzo[7]annulene (0.279 mmol, 1.0 equiv.), ammonium carbamate (1.1172 mmol, 4 equiv.), oxalic acid (1.67 mmol, 6 equiv.), $PdCl_2$ (0.013 mmol, 0.05 equiv.), dppe (0.013 mmol, 0.05 equiv.), TBACl (0.139 mmol, 0.50 equiv.) in DMF and t-amyl alcohol in 1:1 ratio (0.5:0.5 ml) was placed in a pressurized reaction tube (5 ml) under conventional heating (130° C.) for 20 hrs. After cooling to ambient temperature, water was added to the reaction mixture and extracted with ethyl acetate (3×10 ml). The combined organic layer was washed with water and dried over $Na_2SO_4$ and solvent was removed under reduced pressure. The viscous liquid obtained was purified by column chromatography on silica gel (60-120 mesh) using hexane: EtOAc (70:30) to afford the desired product as a yellow solid (20 mg, 30%). 1H NMR (CDCl3, 600 MHz, δ, ppm): 1.25 (s, 6H), 1.76-1.74 (t, J=6.66 Hz, 2H), 2.31 (s, 3H), 2.50-2.46 (m, 2H), 4.25 (s, 2H), 7.07-7.06 (d, J=7.92 Hz, 1H), 7.27 (s, 1H), 7.38-7.37 (d, J=7.98 Hz, 1H); 13C NMR (CDCl3, 150 MHz, δ, ppm): 21.5, 24.1, 28.9, 36.4, 38.0, 47.9, 126.7, 127.2, 128.2, 128.3, 133.4, 138.4, 146.6, 150.5, 174.1. ESI-MS: calcd for $C_{16}H_{19}NO_2$ $[M+H]^+$ 242.1539, found 242.1002.

Formula II (b)

Synthesis of 2-benzyl-6,6,8-trimethyl-1,4,5,6-tetrahydrobenzo[3,4]cyclohepta[1,2-c]pyrrol-3(2H)-one

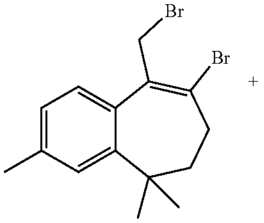

-continued

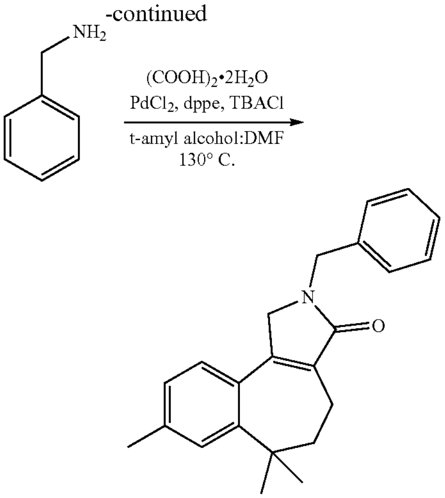

A mixture of 8-bromo-9-(bromomethyl)-3,5,5-trimethyl-6,7-dihydro-5H-benzo[7]annulene (0.279 mmol, 1.0 equiv.), phenylmethanamine (1.1172 mmol, 1.2 equiv.), oxalic acid (1.67 mmol, 6 equiv.), $PdCl_2$ (0.013 mmol, 0.05 equiv.), dppe (0.013 mmol, 0.05 equiv.), TBACl (0.139 mmol, 0.50 equiv.) in DMF and t-amyl alcohol in 1:1 ratio (0.5:0.5 ml) was placed in a pressurized reaction tube (5 ml) under conventional heating (130° C.) for 20 hrs. After cooling to ambient temperature, water was added to the reaction mixture and extracted with ethyl acetate (3×10 ml). The combined organic layer was washed with water and dried over $Na_2SO_4$ and solvent was removed under reduced pressure. The viscous liquid obtained was purified by column chromatography on silica gel (60-120 mesh) using hexane: EtOAc (70:30) to afford the desired product as a semisolid (25%). 1H NMR (CDCl3, 600 MHz) δ 1.34 (s, 6H), 1.90-1.88 (t, J=6.6 Hz, 2H), 2.36 (s, 3H), 2.77-2.75 (t, J=6.5 Hz, 2H), 4.19 (s, 2H), 4.73 (s, 2H), 7.01-7.00 (d, J=7.3 Hz, 1H), 7.18-7.16 (d, J=7.9 Hz, 1H), 7.32-7.28 (m, 4H), 7.38-7.35 (m, 2H); 13C NMR (CDCl3, 150 MHz,) δ 22.01, 24.94, 29.38, 36.68, 38.57, 46.68, 52.70, 127.23, 127.34, 127.91, 128.04, 128.21, 128.56, 129.27, 134.08, 137.4, 137.91, 139.20, 144.77, 151.25, 172.68. ESI-MS: calcd. for $C_{23}H_{25}NO$ $[M+H]^+$=332.2009, found 331.8708.

Example 4

General Procedure for the Synthesis of Formula IV

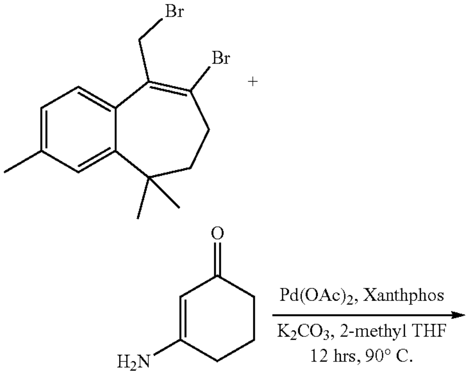

-continued

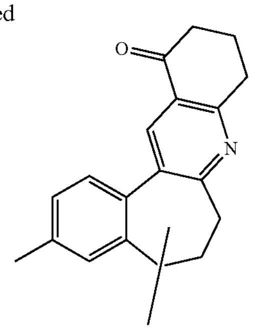

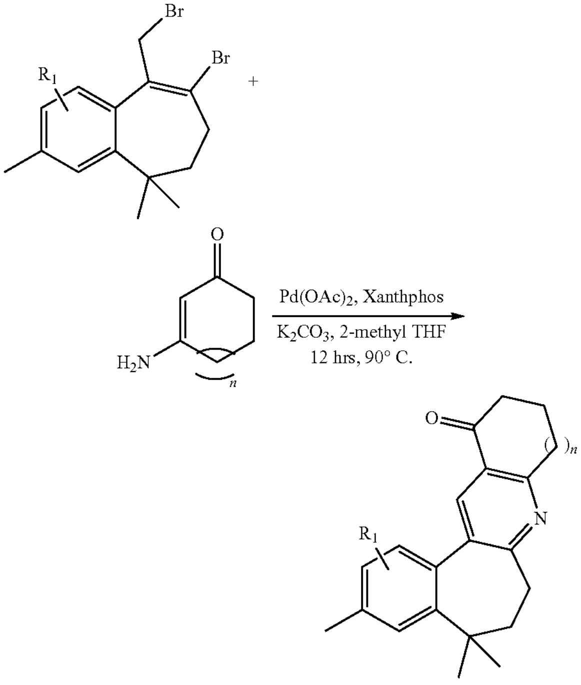

n = 5, 6

Formula IV (a)

Synthesis of 3,5,5-trimethyl-5,6,7,9,10,11-hexahydro-12H-benzo[3,4]cycloheptal[1,2-b]naphthalene-12-one A mixture of 8-bromo-9-(bromomethyl)-3,5,5-trimethyl-6,7-dihydro-5H-benzo[7]annulene (0.279 mmol, 1.0 equiv.), 3-amino-2-cyclohexen-1-one/3-aminocyclopent-2-en-1-one (0.33 mmol, 1.2 equiv.), Pd(OAc)2 (0.055 mmol, 20 mol %), Xanthphos (0.055 mmol, 20 mol %), $K_2CO_3$ (0.55 mmol, 2 equvi.) in 2-methyl THF (1.5 ml) were placed in reaction tube (15 mL) at 90° C. for 12 h. After cooling the reaction mixture to ambient temperature, water was added and extracted with ethyl acetate (10×3 times). The combined organic layer was washed with water and dried over $Na_2SO_4$ and vacuum evaporated. The viscous liquid obtained which was purified by column chromatography on silica gel (mesh 60-120) using the mixture of hexane: EtOAc (80:20) to obtained the desired product as semisolid (38 mg, 45%).

$^1H$ NMR ($CDCl_3$, 600 MHz, δ, ppm): 1.18 (s, 6H), 2.18-2.13 (m, 4H), 2.35 (s, 3H), 2.66-2.62 (m, 2H), 2.76-2.71 (t, J=7.0 Hz, 2H), 3.12-3.08 (t, J=6.1 Hz, 2H), 7.11 (d, 1H), 7.21-7.16 (m, 2H), 8.10 (s, 1H); $^{13}C$ NMR ($CDCl_3$, 150 MHz, δ, ppm): 22.07, 22.7, 29.6, 31.7, 35.5, 37.6, 38.5, 47.3, 126.7, 127.1, 127.3, 130.6, 134.3, 137.3, 138.03, 145.8, 161.5, 164.5, 198.2. ESI-MS: calcd for $C_{21}H_{23}NO$ $[M+H]^+$ 306.1852, found 306.1964.

Formula IV (b)

Synthesis of 3,5,5,10-tetramethyl-5,6,7,9,10,11-hexahydro-12H-benzo[3,4]cyclohepta[1,2-b]quinolin-12-one

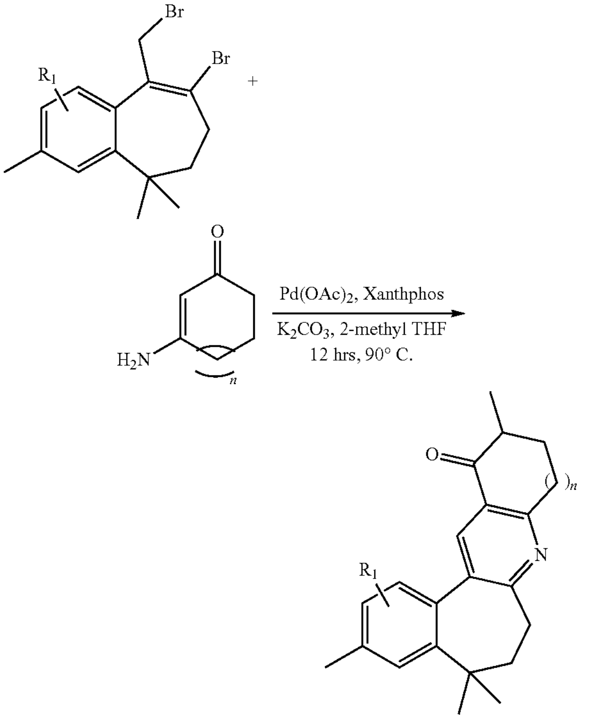

n = 6

A mixture of 8-bromo-9-(bromomethyl)-3,5,5-trimethyl-6,7-dihydro-5H-benzo[7]annulene (0.279 mmol, 1.0 equiv.), 3-amino-2-cyclohexen-1-one/3-amino-6-methylcyclohex-2-en-1-one (0.33 mmol, 1.2 equiv.), Pd(OAc)2 (0.055 mmol, 20 mol %), Xanthphos (0.055 mmol, 20 mol %), $K_2CO_3$ (0.55 mmol, 2 equvi.) in 2-methyl THF (1.5 ml) were placed in reaction tube (15 mL) at 90° C. for 12 h. After cooling the reaction mixture to ambient temperature, water was added and extracted with ethyl acetate (10×3 times). The combined organic layer was washed with water and dried over $Na_2SO_4$ and vacuum evaporated. The viscous liquid obtained which was purified by column chromatography on silica gel (mesh 60-120) using the mixture of hexane: EtOAc (80:20) to obtained the desired product as semisolid (48%).

$^1H$ NMR ($CDCl_3$, 600 MHz, δ, ppm): 1.23 (s, 6H), 1.24 (m, 3H), 2.27-2.24 (m, 4H), 2.45 (s, 3H), 2.91-2.79 (m, 4H), 3.27-3.24 (m, 2H), 3.12-3.08 (t, J=6.1 Hz, 2H), 7.20-7.19 (m, 1H), 7.28-7.27 (m, 1H), 8.18 (s, 1H); $^{13}C$ NMR ($CDCl_3$, 150 MHz, δ, ppm): 21.3, 21.6, 29.5, 31.7, 35.6, 37.6, 40.6, 46.7, 47.3, 126.5, 126.7, 127.4, 130.6, 132.6, 134.3, 137.2, 138.0, 145.8, 161.0, 164.6, 198.3. ESI-MS: calcd for $C_{22}H_{25}NO$ $[M+H]^+$ 320.2009, found 320.1964.

Example 5

General Procedure for the Synthesis of Formula VI

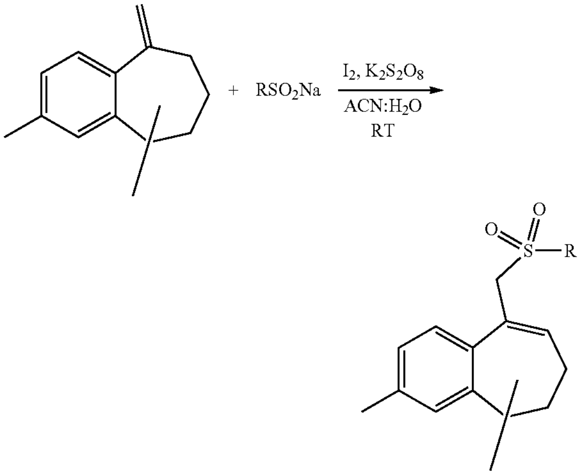

R = Alkyl

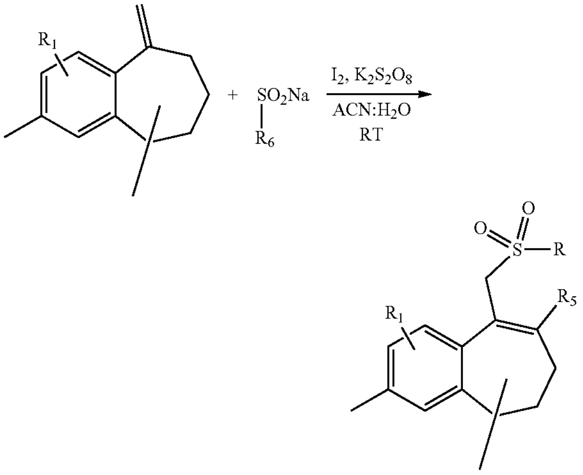

R6 = Aryl, alkyl
R5 = hydrogen

Formula VI (a)

Synthesis of 3,5,5-Trimethyl-9-((phenylsulfonyl) methyl)-6,7-dihydro-5H-benzo[7]annulene A mixture of 2,9,9-trimethyl-5-methylene-6,7,8,9-tetrahydro-5H-benzo[7]annulene (0.25 mmol, 1.0 equiv.), sodium benzenesulfinate (0.3 mmol, 1.2 equiv.), $K_2S_2O_8$ (0.62 mmol, 2.5 equiv.), and $I_2$ (0.3 mmol, 1.2 equiv.), in ACN:$H_2O$ (1:1) were placed in reaction tube (5 mL) at room temperature for 12 h. After completion of reaction, a saturated solution of sodium thiosulfate was added to the reaction mixture and extracted with ethyl acetate (10×3 times). The combined organic layer was washed with water and dried over $Na_2SO_4$ and vacuum evaporated. The viscous liquid obtained was purified by column chromatography on silica gel (mesh 60-120) using the mixture of hexane: EtOAc (80:20) to obtained the desired product as semisolid (71 mg, 84%).

$^1H$ NMR ($CDCl_3$, 600 MHz) δ 1.34 (s, 6H), 1.96-1.99 (t, J=7.2 Hz, 2H), 2.10-2.12 (t, J=6.9 Hz, 2H), 2.34 (s, 3H), 4.22 (s, 2H), 6.24-6.26 (t, J=6.4 Hz, 1H), 6.95 (d, J=7.8 Hz, 1H), 7.20 (d, J=8.1 Hz, 2H), 7.51-7.53 (t, J=7.8 Hz, 2H), 7.61-7.64 (m, 1H), 7.90 (d, J=7.5 Hz, 2H); $^{13}C$ NMR ($CDCl_3$, 150 MHz) δ 21.3, 27.0, 30.8, 38.0, 46.5, 63.7, 126.4, 126.5, 128.1, 128.3, 128.4, 129.0, 133.4, 134.4, 136.6, 137.0, 139.7, 148.0. ESI-MS: calcd. for $C_{21}H_{24}O_2S$ $[M+H]^+$ 341.1575, found 341.1565.

Formula VI(b)

Synthesis of 3,5,5-trimethyl-9-(tosylmethyl)-6,7-dihydro-5H-benzo[7]annulene

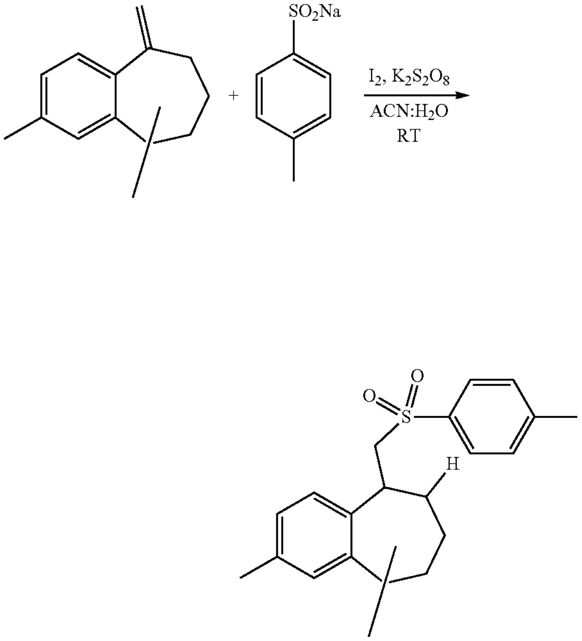

A mixture of 2,9,9-trimethyl-5-methylene-6,7,8,9-tetrahydro-5H-benzo[7]annulene (0.25 mmol, 1.0 equiv.), sodium 4-methylbenzenesulfinate (0.3 mmol, 1.2 equiv.), $K_2S_2O_8$ (0.62 mmol, 2.5 equiv.), and $I_2$ (0.3 mmol, 1.2 equiv.), in ACN:$H_2O$ (1:1) were placed in reaction tube (5 mL) at room temperature for 12 h. After completion of reaction, a saturated solution of sodium thiosulfate was added to the reaction mixture and extracted with ethyl acetate (10×3 times). The combined organic layer was washed with water and dried over $Na_2SO_4$ and vacuum evaporated. The viscous liquid obtained was purified by column chromatography on silica gel (mesh 60-120) using the mixture of hexane: EtOAc (80:20) to obtained the desired product as semisolid (64 mg, 72%).

1H NMR ($CDCl_3$, 600 MHz) δ 1.35 (s, 6H), 1.97-2.00 (t, J=7.2 Hz, 2H), 2.11-2.14 (m, 2H), 2.35 (s, 3H), 2.45 (s, 3H), 4.21 (s, 2H), 6.24-6.27 (t, J=6.5 Hz, 1H), 6.96-6.97 (d, J=7.3 Hz, 1H), 7.21-7.24 (t, J=8.5 Hz, 2H), 7.31-7.32 (d, J=8.1 Hz, 2H), 7.78-7.79 (d, J=8.2 Hz, 2H); 13C NMR ($CDCl_3$, 150 MHz) δ 21.49, 21.65, 27.12, 30.92, 38.09, 46.69, 63.88, 126.46, 126.62, 128.38, 128.43, 128.60, 129.71, 134.63, 136.57, 136.79, 136.85, 144.50, 148.08. ESI-MS: calcd. For $C_{22}H_{26}O_2S$ $[M+H]^+$ 355.1732, found 355.1720.

Formula VI (c)

Synthesis of 3,5,5-Trimethyl-9-((methylsulfonyl) methyl)-6,7-dihydro-5H-benzo[7]annulene

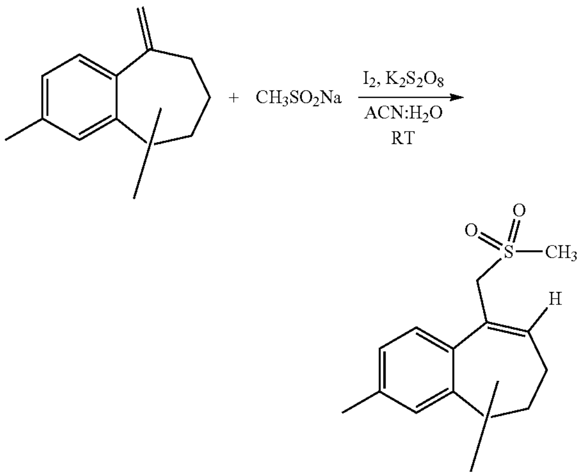

A mixture of 2,9,9-trimethyl-5-methylene-6,7,8,9-tetrahydro-5H-benzo[7]annulene (0.25 mmol, 1.0 equiv.), sodium methanesulfinate (0.3 mmol, 1.2 equiv.), $K_2S_2O_8$ (0.62 mmol, 2.5 equiv.), and 12 (0.3 mmol, 1.2 equiv.), in ACN:$H_2O$ (1:1) were placed in reaction tube (5 mL) at room temperature for 12 h. After completion of reaction, a saturated solution of sodium thiosulfate was added to the reaction mixture and extracted with ethyl acetate (10×3 times). The combined organic layer was washed with water and dried over $Na_2SO_4$ and vacuum evaporated. The viscous liquid obtained was purified by column chromatography on silica gel (mesh 60-120) using the mixture of hexane: EtOAc (60:40) to obtained the desired product as semisolid (42 mg, 60%).

$^1$H NMR ($CDCl_3$, 600 MHz) δ 1.40 (s, 6H), 2.00-2.02 (t, J=7.0 Hz, 2H), 2.20-2.23 (m, 2H), 2.37 (s, 3H), 2.71 (s, 3H), 4.19 (s, 2H), 6.40-6.42 (t, J=6.2 Hz, 1H), 7.09 (d, J=7.8 Hz, 1H), 7.27 (s, 1H), 7.32 (d, J=7.8 Hz, 1H); $^{13}$C NMR ($CDCl_3$, 150 MHz) δ 21.39, 27.18, 30.58, 38.09, 41.10, 45.98, 62.80, 126.74, 127.04, 127.96, 128.12, 133.68, 137.12, 137.40, 148.54. ESI-MS: calcd. for $C_{16}H_{22}O_2S$ $[M+H]^+$ 279.1419, found 279.1410.

Example 6

General Procedure for the Synthesis of Formula V

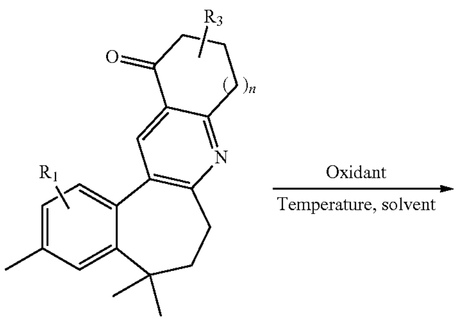

-continued

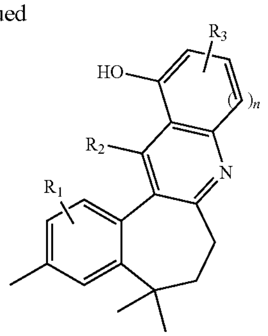

n = 5, 6
$R^3$ = alkyl

Synthesis of 3,5,5,10-tetramethyl-6,7-dihydro-5H-benzo[3,4]cyclohepta[1,2-b]quinolin-12-ol A mixture of 3,5,5,10-tetramethyl-5,6,7,9,10,11-hexahydro-12H-benzo[3,4]cyclohepta[1,2-b]quinolin-12-one (1.0 equiv.), oxidant (0.3 mmol, 2 equiv.) in solvent (1:1) were placed in reaction tube (5 mL) for 12 h. After cooling the reaction mixture to ambient temperature, water was added and extracted with ethyl acetate (10×3 times). The combined organic layer was washed with water and dried over $Na_2SO_4$ and vacuum evaporated. The viscous liquid obtained which was purified by column chromatography on silica gel (mesh 60-120) using the mixture of hexane: EtOAc (70:30) to obtained the desired product.

Experimental Procedures

I. Determination of affinity and kinetic constants for PI3K (120y)
II. Determination of affinity of PI3K (120y) inhibitors (KD/IC50) through inhibition in solution assay of kinase PI3K (120y) by various compounds of general formula I-VI
III. Determination of affinity and kinetic constants for MAPKAPK2
IV. Determination of affinity of MK2 inhibitors (IC50) through inhibition in solution assay of kinase MK2 by various compounds of general formula I-VI

Determination of Affinity and Kinetic Constants for PI3K (120y)

Immobilization buffer scouting was performed for PI3K (120y) to find a suitable buffer for immobilization. It was found that 10 mM sodium acetate pH 5.5 buffer is best suitable for the immobilization. Immobilization of the PI3K (120y) kinase was performed at 25° C. temperature using concentration of Kinase 5 μg/ml with a flow rate of 10 μl/min and 1000 sec of contact time. Successful immobilization of 9191.2 RU of kinase PI3K (120y) over flow cell 4 of sensor surface CM5 by amine coupling was achieved.

After immobilization, kinetics screening for binding of compounds with PI3K (120y) was performed with the protocol recommended as per Biacore Assay Handbook (protocol: kinetic screening using a single concentration of compounds, concentration used: 50 μMin 1×PBS with 5% DMSO, running buffer: 1×PBS with 5% DMSO, temperature: 25° C., buffer blanks: 1×PBS with 5% DMSO wizard used: Kinetics/Affinity). Compound K were prepared in 50 μM concentration in 1× PBS with 5% DMSO and placed in sample compartment at 25° C. These were passed over the sensor through flow cell 1 (reference-blank) and 2 (active-immobilized with kinase) in flow rate of 30 μl/min at 25° C. Binding responses were seen in real time for Fc 2 (active), Fc1 (reference) and Fc 2-1 (reference subtracted). Solvent correction was done for DMSO (5% in PBS) Data was analyzed using Biacore T200 evaluation software v 3.1 and fitting was done using 1:1 binding model. Also, detailed kinetics characterization was performed for compounds of general formula I.

Figure 2:
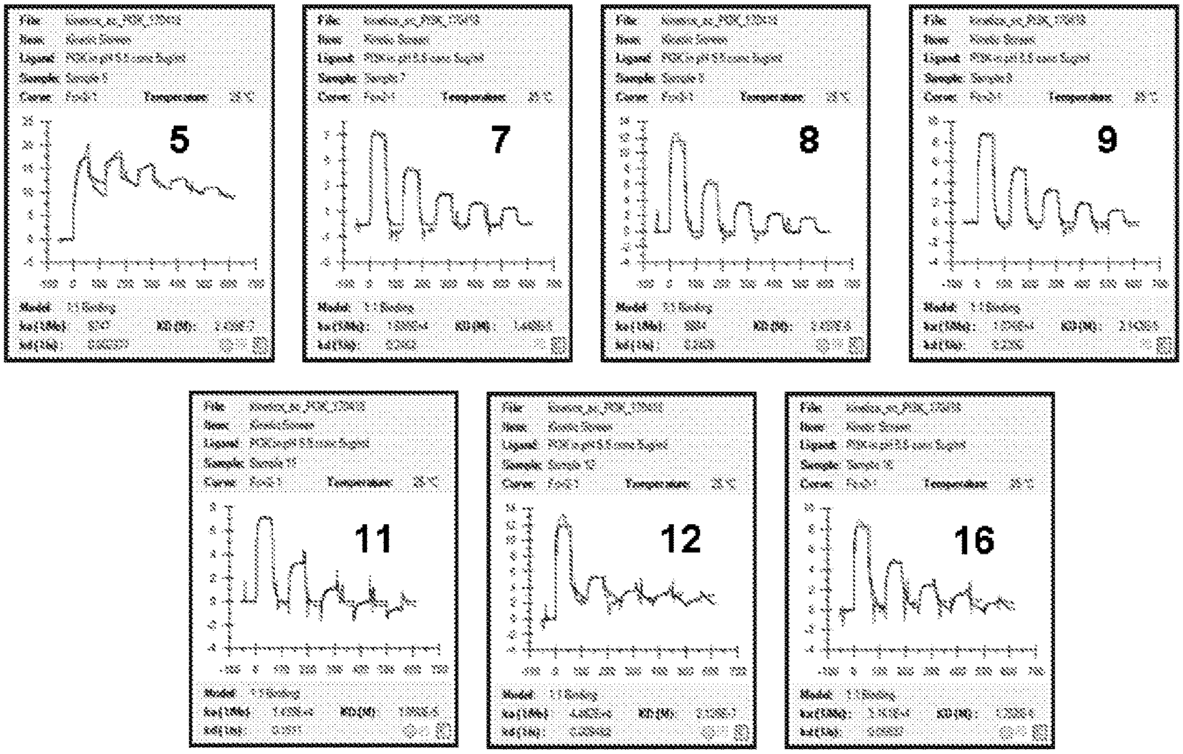
FIG. 2: Graphical representation of the on-rate and off-rate of binding of evaluated compounds of general formula II to PI3K (120y).

Compounds of general formula II showed promising binding and kinetics profiles as shown in FIG. 1, FIG. 2, and Table 1 FIG. 1 depicts the on-rate and off-rate of binding of evaluated compounds of general formula II to PI3K (120y). Plotting association rate constant ka against dissociation rate constant kd (here on logarithmic scales) creates a plot where the affinity is represented by diagonal lines. Compounds on the same diagonal have the same affinity but differ in kinetics. FIG. 2 is the Graphical representation of the on-rate and off-rate of binding of evaluated compounds of general formula II to PI3K (120y).

Table 1 represents the numerical values of binding (on-rate, off-rate and affinity of binding) of evaluated compounds of general formula I to PI3K (120y). KD represents the equilibrium constant of binding in Molar value.

TABLE 1

| Sample | Ka (1/Ms) | Kd (1/s) | KD (M) |
|---|---|---|---|
| Sample 5 | 9.75E+03 | 2.38E−03 | 2.44E−07 |
| Sample 7 | 1.70E+04 | 2.46E−01 | 1.45E−05 |
| Sample 8 | 9.88E+03 | 2.41E−01 | 2.44E−05 |
| Sample 9 | 1.08E+04 | 2.31E−01 | 2.14E−05 |
| Sample 11 | 1.44E+04 | 1.51E−01 | 1.05E−05 |
| Sample 12 | 4.46E+04 | 9.48E−03 | 2.13E−07 |
| Sample 16 | 3.16E+04 | 5.54E−02 | 1.75E−06 |

Detailed kinetics characterization of selected compounds (Compounds having general formula II that is pyrolone fused benzocycloheptene) for binding to PI3K (120y) were performed using the protocol recommended as per Biacore Assay Handbook (protocol: kinetic analysis using single cycle kinetics method, concentrations used: 10, 5, 2.5, 1.25, 0.625 μM in 1×PBS with 5% DMSO, running buffer: 1×PBS with 5% DMSO, temperature: 25° C. Buffer blanks: 1×PBS with 5% DMSO, wizard used: Kinetics/Affinity). Compound (Compounds having general formula II that is pyrolone fused benzocycloheptene) were prepared in 10 μM concentration in 1× PBS with 5% DMSO and serial diluted to make 5, 2.5, 1.25 and 0.625 μM concentration. They were placed in sample compartment at 25° C. These were passed over the sensor through flow cell 1 (reference-blank) and 2 (active-immobilized with kinase) in flow rate of 30 μl/min at 25° C. using single cycle kinetics injection method. Binding responses were seen in real time for Fc2 (active), Fc1 (reference) and Fc 2-1 (reference subtracted). Solvent correction was done for DMSO (5% in PBS). Data was analyzed using Biacore T200 evaluation software v 3.1. Fitting of data is done using 1:1 binding model and kinetics constants as well as equilibrium kinetics constant of dissociation (KD) was also determined.

Figure 3:
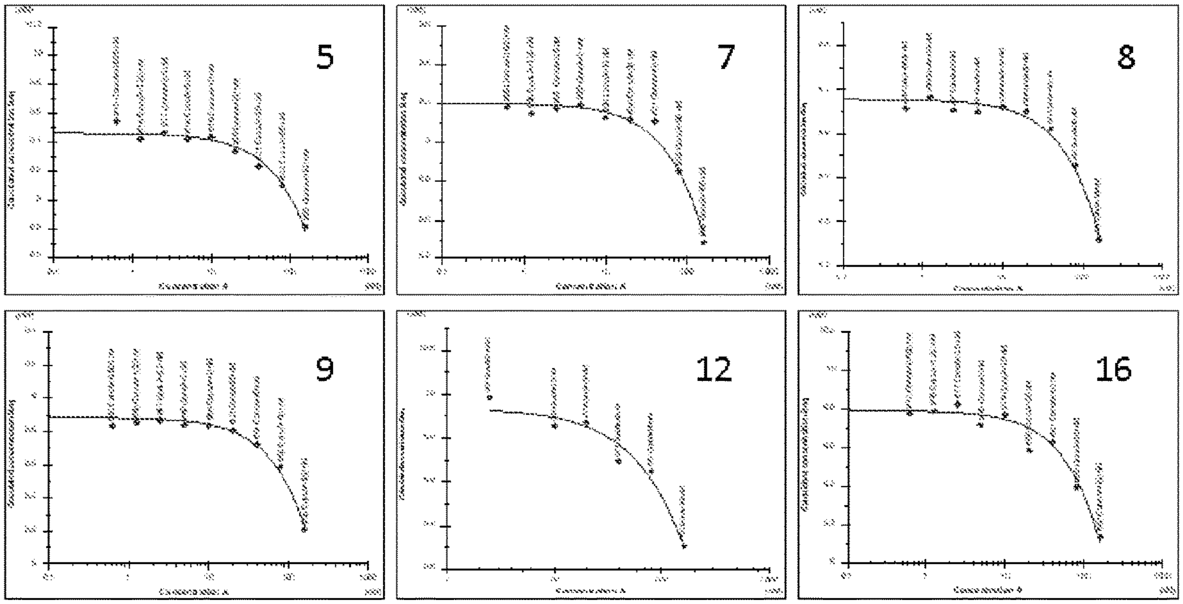
FIG. 3: Graphs represent the dose dependent inhibition of the PI3K (120y) by compounds of general formula II (5, 7, 8, 9, 12 and 16).

Compounds of general formula II showed effective inhibitory potential against PI3K (120y) with IC50 ranging in between 2-2.5 μM as provided in FIG. 3, and Table 2. FIG. 3 represents the dose dependent inhibition of the PI3K (120y) by compounds of general formula II (5, 7, 8, 9, 12 and 16). Table 2: Table represents the extrapolated IC50 values of the compounds of general formula I against the PI3K(120y) from the graphs.

TABLE 2

| S. No. | Ligand (Small Molecules) | IC50 |
|---|---|---|
| 1 | Ligand 5 | 2057 nM |
| 2 | Ligand 7 | 1958 nM |
| 3 | Ligand 8 | 2173 nM |
| 4 | Ligand 9 | 1999 nM |
| 6 | Ligand 12 | 2342 nM |
| 7 | Ligand 16 | 2093 nM |

Example 7

Determination of Affinity and Kinetic Constants for Mk2

Immobilization buffer scouting was performed for MK2 to find suitable buffer for immobilization and it was found that 10 mM Sodium acetate pH 5.5 buffer is best suitable for the immobilization. Immobilization of the MK2 kinase was performed at 25° C. temperature using concentration of Kinase 10 μg/ml with a flow rate of 10 μl/min and 1000 sec of contact time. Successful immobilization of 11119.6 RU of kinase MK2 over flow cell 4 of sensor surface CM5 by amine coupling was achieved.

After immobilization, kinetics screening for binding of compounds with MK2 was performed with the protocol recommended as per Biacore Assay Handbook (protocol: kinetic screening using a single concentration of compounds, concentration used: 50 μM in 1×PBS with 5% DMSO, running buffer: 1×PBS with 5% DMSO, temperature: 25° C., buffer blanks: 1×PBS with 5% DMSO wizard used: Kinetics/Affinity). Compound (Compounds having general formula II that is pyrolone fused benzocycloheptene) were prepared in 50 μM concentration in 1× PBS with 5% DMSO and placed in a sample compartment at 25° C. These were passed over the sensor through flow cell 3 (reference-blank) and 4 (active-immobilized with kinase) in flow rate of 30 μl/min at 25° C. Binding responses were seen in real time for Fc 4 (active), Fc3 (reference) and Fc 4-3 (reference subtracted). Solvent correction was done for DMSO (5% in PBS). Data was analyzed using Biacore T200 evaluation software v 3.1 and fitting was done using 1:1 binding model.

Figure 4:
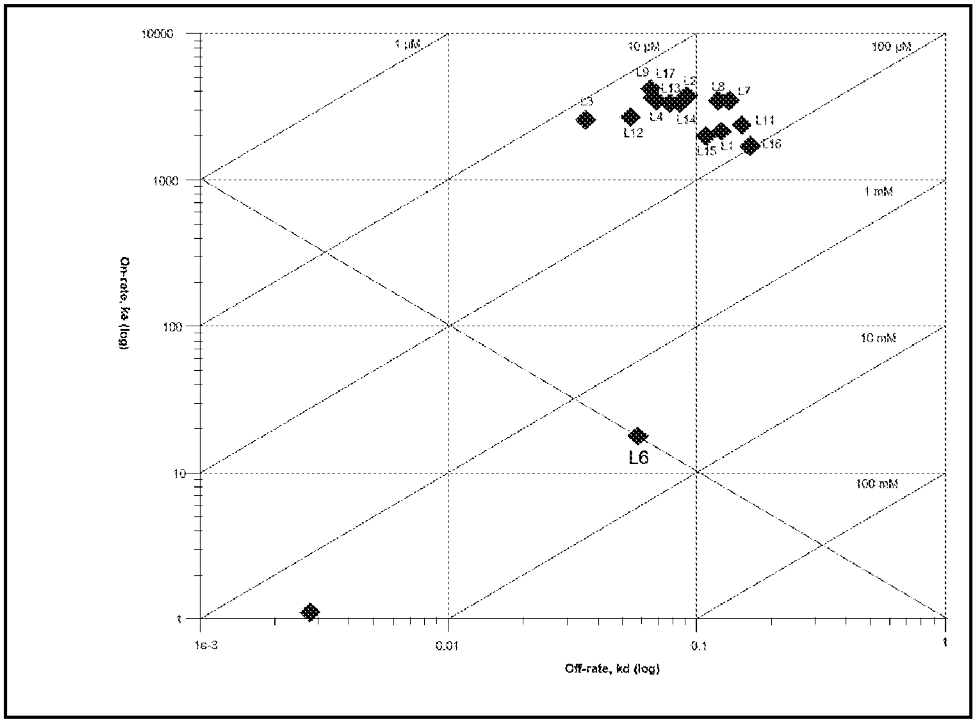
FIG. 4: Image depicts the on-rate and off-rate of binding of evaluated compounds of general formula II to MK2. Plotting association rate constant ka against dissociation rate constant kd (here on logarithmic scales) creates a plot where the affinity is represented by diagonal lines. Compounds on the same diagonal have the same affinity but differ in kinetics.
Figure 5:
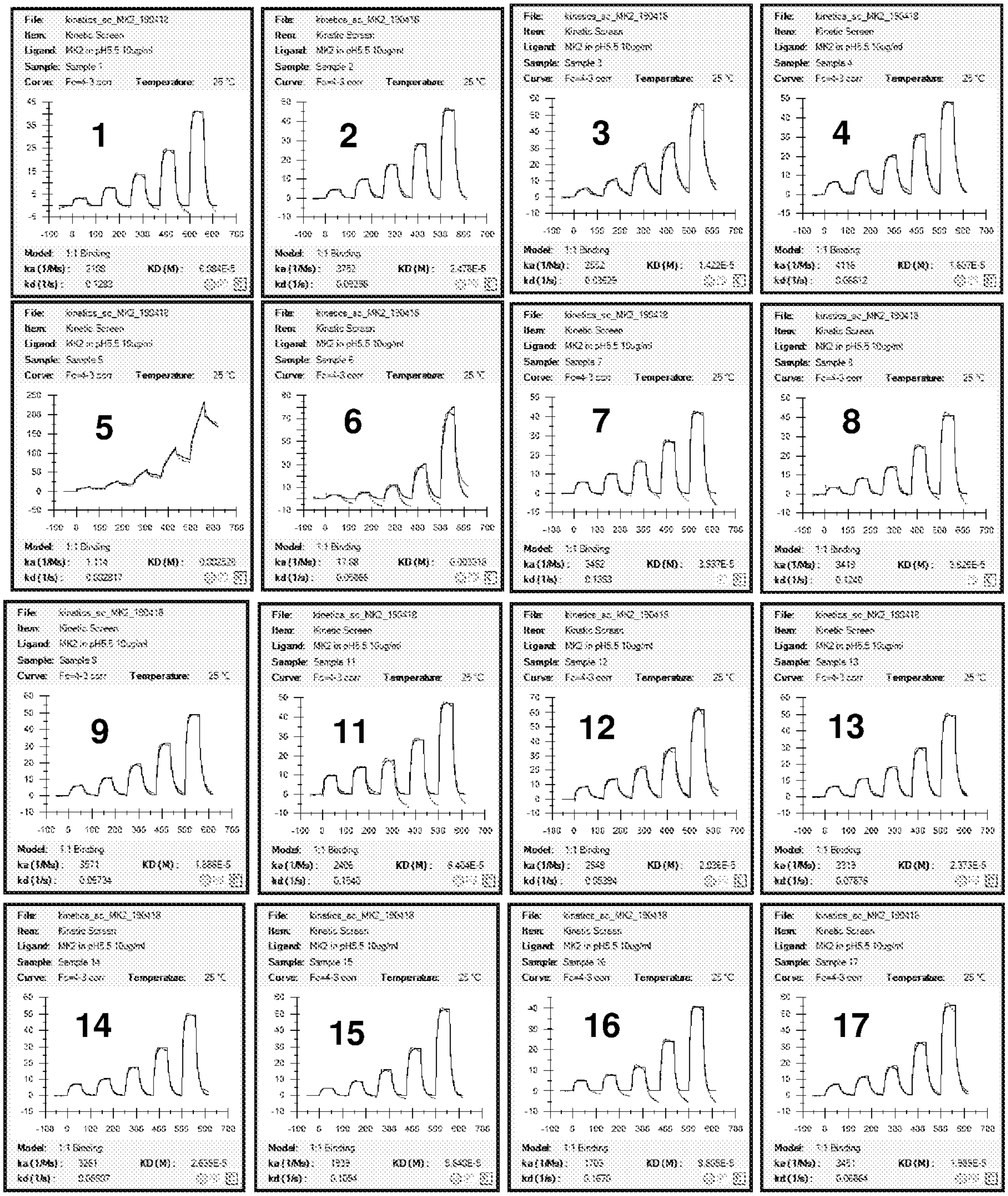
FIG. 5: Graphical representation of the on-rate and off-rate of binding of evaluated compounds of general formula II to MK2

Compounds of general formula II showed promising binding and kinetics profiles. Out of them, on the basis of their binding and kinetic profiles, 9 most promising lead compounds of general formula II along with one marketed MK2-inhibitor compound (PF 3644022) were selected for further in-solution inhibition assay. The results are provided in FIG. 4, FIG. 5, and Table 3. FIG. 4 depicts the on-rate and off-rate of binding of evaluated compounds of general formula II to MK2. Plotting association rate constant ka against dissociation rate constant kd (here on logarithmic scales) creates a plot where the affinity is represented by diagonal lines. Compounds on the same diagonal have the same affinity but differ in kinetics. FIG. 5 is the graphical representation of the on-rate and off-rate of binding of evaluated compounds of general formula II to MK2. Table 3 represents the numerical values of binding (on-rate, off-rate and affinity of binding) of evaluated compounds of general formula II to MK2. KD represents the equilibrium constant of binding in Molar value.

TABLE 3

| Sample | Ka (1/Ms) | Kd (1/s) | KD (M) |
|---|---|---|---|
| Sample 1 | 2.11E+03 | 1.28E−01 | 6.08E−05 |
| Sample 2 | 3.75E+03 | 9.30E−02 | 2.48E−05 |
| Sample 3 | 2.55E+03 | 3.63E−02 | 1.42E−05 |
| Sample 4 | 4.12E+03 | 6.61E−02 | 1.61E−05 |
| Sample 5 | 1.11E+00 | 2.82E−03 | 2.53E−03 |
| Sample 6 | 1.77E+01 | 5.87E−02 | 3.32E−03 |
| Sample 7 | 3.46E+03 | 1.36E−01 | 3.94E−05 |
| Sample 8 | 3.42E+03 | 1.24E−01 | 3.63E−05 |
| Sample 9 | 3.57E+03 | 6.73E−02 | 1.89E−05 |
| Sample 11 | 2.41E+03 | 1.54E−01 | 6.40E−05 |
| Sample 12 | 2.65E+03 | 5.39E−02 | 2.04E−05 |
| Sample 13 | 3.32E+03 | 7.88E−02 | 2.37E−05 |
| Sample 14 | 3.26E+03 | 8.61E−02 | 2.64E−05 |
| Sample 15 | 1.94E+03 | 1.09E−01 | 5.64E−05 |
| Sample 16 | 1.70E+03 | 1.67E−01 | 9.81E−05 |

Detailed kinetics characterization of selected compounds binding to MK2 were performed using the protocol recommended as per Biacore Assay Handbook (protocol: kinetic analysis using single cycle kinetics method, concentrations used: 30, 15, 7.5, 3.75, 1.87 μMin 1×PBS with 5% DMSO, running buffer: 1×PBS with 5% DMSO, temperature: 25° C., buffer blanks: 1×PBS with 5% DMSO, wizard used: Kinetics/Affinity). Compounds were prepared in 30 μM concentration in 1× PBS with 5% DMSO and serial diluted to make 15, 7.5, 3.75 and 1.87 μM concentration. They were placed in a sample compartment at 25° C. These were passed over the sensor through flow cell 3 (reference-blank) and 4 (active-immobilized with kinase) in flow rate of 30 μl/min at 25° C. using single cycle kinetics injection method. Binding responses were observed in real time for Fc 4 (active), Fc3 (reference) and Fc 4-3 (reference subtracted). Solvent correction was done for DMSO (5% in PBS). Data was analyzed using Biacore T200 evaluation software v 3.1 and fitting of data was done using 1:1 binding model and kinetics constants as well as equilibrium kinetics constant of dissociation (KD) was also determined.

Compounds of general formula II showed effective inhibitory potential against MK2 with IC50 between ranging in between 526-709 nM. The values are in well competence with IC50 value of marketed MK2-inhibitor (585 nM) as provided in FIG. 6, and Table 4.

Figure 6:
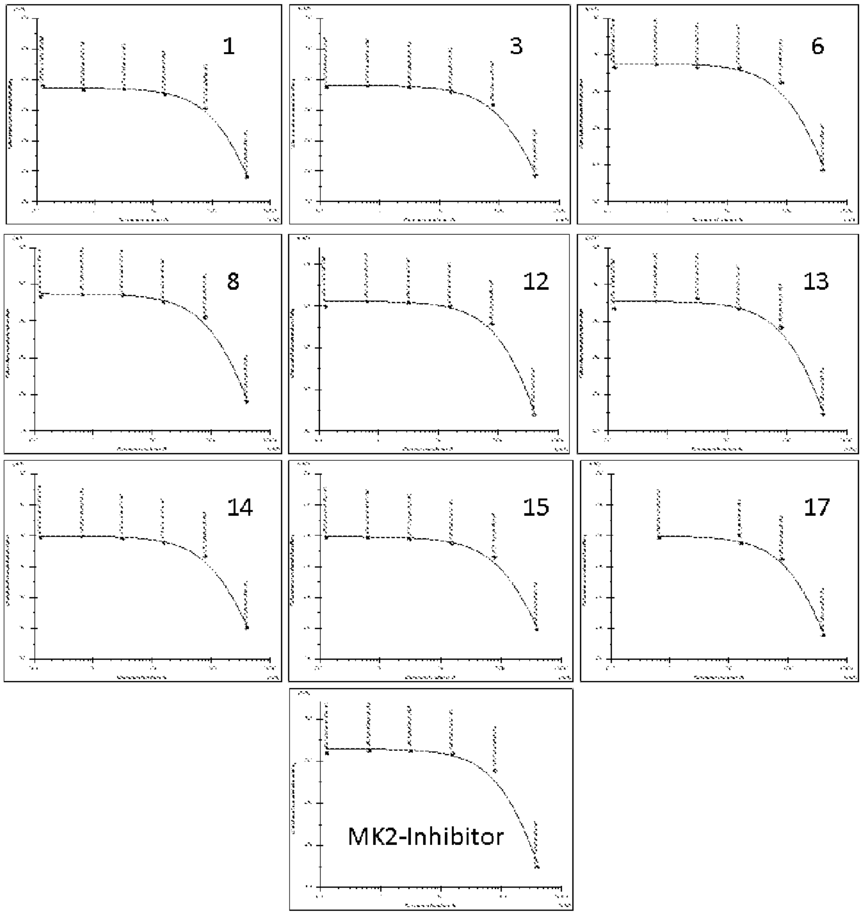
FIG. 6: Graphs represent the dose dependent inhibition of the MK2 by compounds of general formula II (1, 3, 6, 8, 12, 13, 14, 15 and 17 along with marketed MK2-inhibitor PF 3644022.

FIG. 6: Graphs represent the dose dependent inhibition of the MK2 by compounds of general formula II (1, 3, 6, 8, 12, 13, 14, 15 and 17 along with marketed MK2-inhibitor PF 3644022. Table 4 represents the extrapolated IC50 values of the compounds of general formula II against MK2 from the graphs.

TABLE 4

| S. No. | Ligand (Small Molecules) | IC50 |
|---|---|---|
| 1 | Ligand 1 | 650 nM |
| 2 | Ligand 3 | 526 nM |
| 3 | Ligand 6 | 550 nM |
| 4 | Ligand 8 | 525 nM |
| 5 | Ligand 12 | 709 nM |
| 6 | Ligand 13 | 578 nM |
| 7 | Ligand 14 | 545 nM |
| 8 | Ligand 15 | 531 nM |
| 9 | Ligand 17 | 596 nM |
| 10 | Marketed MK2 Inhibitor (PF 3644022) | 585 nM |

Advantages of the Invention

The main scaffold of benzocycloheptene comes from natural precursor. Therefore, use of natural precursor reduces the number of steps for the synthesis of the compounds.

The cost of obtaining plant derived precursor is very low, as the plant is abundant in nature, hence the overall process is economic.

The process is also sustainable as 60-80% of the molecules come from natural precursor and only 40-20% molecule were used through synthetic process.

The compounds of general formula I-VI are less toxic.

The compound of general formula I-VI are applicable for treatment of PI3K and MK2 related disorder.

We claim:

1. A compound of formula (I), (II), (III), (IV), (V), or (VI):

I

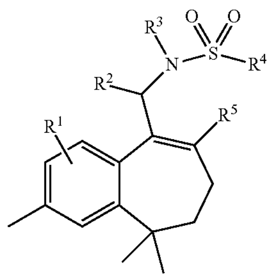

II

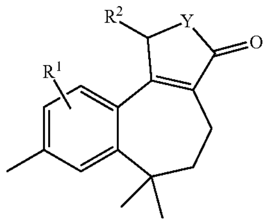

III

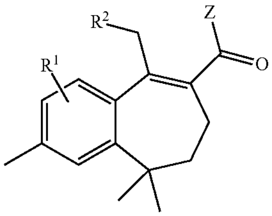

IV

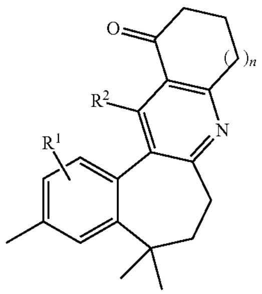

-continued

V

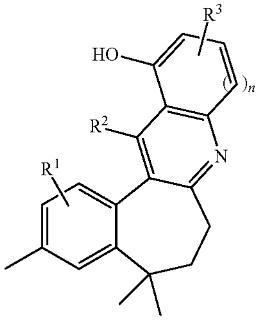

VI

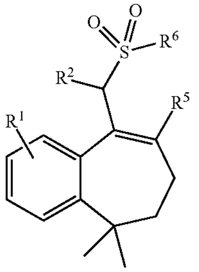

or a pharmaceutical acceptable salt or enantiomer thereof, wherein, in each of formulas (I), (II), (III), (IV), (V), and (VI):

Y is selected from the group consisting of carbon, nitrogen, oxygen, and sulfur;

Z is selected from the group consisting of —H, C1-C6 alkyl, C1-C6 aryl, halogen, oxygen, nitrogen, and sulfur;

$R^1$ is selected from the group consisting of —H, —OH, N-substituted benzylamine, N- substituted aniline, S-substituted thiophenes, carboxylic acids, and halogen;

$R^2$ is selected from the group consisting of —H, C1-C6 alkyl, C1-C6 aryl, halogen, C1-C6 amine, and C1-C6 carbonyl groups;

$R^3$ is selected from the group consisting of —H, C1-C6 alkyl, C1-C6 aryl, and thiophenes;

X is selected from the group consisting of carbon, nitrogen, oxygen, and sulfur;

$R^4$ is selected from the group consisting of —H, C1-C6 alkyl, C1-C6 aryl, halogen, and aldehyde-substituted benzenesulfonamides;

$R^5$ is selected from the group consisting of —H, C1-C6 alkyl, C1-C6 aryl, halogen, and C1-C6 carbonyl group; and $R^6$ is selected from the group consisting of —H, C1-C6 alkyl, C1-C6 aryl, and C1-C6 amine group.

2. The compound of claim 1, wherein the compound has formula (I), where:

$R^1$ is selected from the group consisting of —H, —OH, N-substituted benzylamine, N-substituted anilines, carboxylic acids, and halogens, $R^2$ is selected from the group consisting of H, C1-C6 alkyl, C1-C6 aryl, halogen, C1-C6 amine, and C1-C6 carbonyl group; and $R^3$, $R^4$, and $R^5$ are each independently selected from the group consisting of —H, C1-C6 alkyl, C1-C6 aryl, halogen, and C1-C6 carbonyl group.

3. The compound of claim 1, wherein the compound has formula (II), where:

$R^1$ is selected from the group consisting of —H, OH, N-substituted benzylamine, N-substituted aniline, carboxylic acids, and halogen, $R^2$ is selected from the group consisting of —H, C1-C6 alkyl, C1-C6 aryl, halogen, C1-C6 amine, and C1-C6 carbonyl; and Y is selected from the group consisting of carbon, oxygen, nitrogen, and sulfur.

4. The compound of claim 1, wherein the compound has formula (III), where:

$R^1$ is selected from the group consisting of —H, 13 OH, benzylamine, aniline, carboxylic acids, and halogen;

$R^2$ is selected from the group consisting of —H, C1-C6 alkyl, C1-C6 aryl, halide, C1-C6 amine, and C1-C6 carbonyl; and Z is selected from the group consisting of —H, C1-C6 alkyl, C1-C6 aryl, halogen, oxygen, nitrogen, and sulfur.

5. The compound of claim 1, wherein the compound has formula (IV), where:

$R^1$ is selected from the group consisting of —H, —OH, N-substituted benzylamine, N-substituted aniline, carboxylic acids, and halogen, $R^2$ is selected from the group consisting of —H, C1-C6 alkyl, C1-C6 aryl, halogen, C1-C6 amine, and C1-C6 carbonyl; and n is 5 or 6.

6. The compound of claim 1, wherein the compound has the formula (V), where:

$R^1$ is selected from the group consisting of —H, 13 OH, N-substituted benzylamine, N-substituted aniline, carboxylic acids, and halogen;

$R^2$ is selected from the group consisting of —H, C1-C6 alkyl, C1-C6 aryl, halogen, C1-C6 amine, and C1-C6 carbonyl group;

n is from 5 to 6; and $R^3$ is selected from the group consisting of —H, C1-C6 alkyl, C1-C6 aryl, and halogen.

7. The compound of claim 1, wherein the compound has formula (VI), where:

$R^1$ is selected from the group consisting of —H, —OH, N-substituted benzylamine, N-substituted aniline, carboxylic acids, and halogen;

$R^2$ is selected from the group consisting of —H, C1-C6 alkyl, C1-C6 aryl, halogen, C1-C6 amine, and C1-C6 carbonyl;

$R^5$ is selected from the group consisting of hydrogen, C1-C6 alkyl, halogen, sulfur, C1-C6 amine, and C1-C6 aryl; and $R^6$ is selected from the group consisting of —H, C1-C6 alkyl, C1-C6 aryl, and C1-C6 amine.

8. A pharmaceutical formulation comprising the compound according to claim 1 and a pharmaceutically acceptable adjuvant, diluent, or carrier.

9. A method for treating type-2 diabetes or ulcers in a subject, the method comprising administering the compound according to claim 1 to the subject.

10. A method of inhibiting PI3K and MK2 mediated activity in a subject, the method comprising administering the compound according to claim 1 to the subject.

* * * * *